(12) United States Patent
Chaney et al.

(10) Patent No.: US 8,666,128 B2
(45) Date of Patent: Mar. 4, 2014

(54) METHODS, SYSTEMS, AND COMPUTER READABLE MEDIA FOR MAPPING REGIONS IN A MODEL OF AN OBJECT COMPRISING AN ANATOMICAL STRUCTURE FROM ONE IMAGE DATA SET TO IMAGES USED IN A DIAGNOSTIC OR THERAPEUTIC INTERVENTION

(75) Inventors: Edward L. Chaney, Efland, NC (US);
Stephen Pizer, Chapel Hill, NC (US);
Lester Kwock, Chapel Hill, NC (US);
Eric Wallen, Chapel Hill, NC (US);
William Hyslop, Chapel Hill, NC (US);
Robert Broadhurst, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 390 days.

(21) Appl. No.: 12/738,572

(22) PCT Filed: Oct. 20, 2008

(86) PCT No.: PCT/US2008/080504
§ 371 (c)(1),
(2), (4) Date: Oct. 7, 2011

(87) PCT Pub. No.: WO2009/052497
PCT Pub. Date: Apr. 23, 2009

(65) Prior Publication Data
US 2012/0027278 A1    Feb. 2, 2012

Related U.S. Application Data

(60) Provisional application No. 60/999,420, filed on Oct. 18, 2007, provisional application No. 61/087,026, filed on Aug. 7, 2008.

(51) Int. Cl.
*G06K 9/00* (2006.01)
*A61B 5/103* (2006.01)

(52) U.S. Cl.
USPC .......................................... 382/128; 600/587

(58) Field of Classification Search
USPC .............. 382/128–134; 378/4, 8, 21–27, 101;
600/407, 410, 424, 425, 427, 411, 443,
600/449, 587; 128/920, 922
See application file for complete search history.

(56) References Cited

U.S. PATENT DOCUMENTS 5,926,568 A *   7/1999   Chaney et al. ................. 382/217
6,169,817 B1 *  1/2001   Parker et al. ................... 382/131
(Continued)

FOREIGN PATENT DOCUMENTS

JP    2002-177239 A    6/2002
JP    2003-33365 A    2/2003

OTHER PUBLICATIONS

European Search Report for European Patent Application No. 08840167.4 (Sep. 5, 2012).

(Continued)

*Primary Examiner* — Abolfazl Tabatabai
(74) *Attorney, Agent, or Firm* — Jenkins, Wilson, Taylor & Hunt, P.A.

(57) ABSTRACT

Methods, systems, and computer readable media for mapping a model of an object comprising an anatomical structure in a planning image and an intervention target region within it to intervention-guiding image data are disclosed. According to one method, an initial medial representation object model (m-rep) of an object comprising an anatomical structure is created based on image data of at least a first instance of the object. A patient-specific m-rep is created by deforming the initial m-rep based on planning image data of at least a second instance of the object, wherein the at least second instance of the object is associated with the patient. An intervention target region within the m-rep is identified in an image registered with the planning image. The patient-specific m-rep is correlated to the intervention-guiding image data of the at least second instance of the object, deformed from the planning image. The intervention target region is transferred to the intervention-guiding image according to the transformation between the m-rep in the planning image and the m-rep in the intervention-guiding image.

41 Claims, 17 Drawing Sheets

(56) References Cited

U.S. PATENT DOCUMENTS

| | | | |
|---|---|---|---|
| 7,200,251 B2* | 4/2007 | Joshi et al. | 382/128 |
| 7,831,293 B2* | 11/2010 | Ellis et al. | 600/424 |
| 2003/0156111 A1 | 8/2003 | Joshi et al. | |
| 2006/0184003 A1 | 8/2006 | Lewin et al. | |

OTHER PUBLICATIONS

Berg-Foels et al., "Femoral head secondary center of ossification shape development in a canine model of hip dysplasia: onset, mineral density, and shape," Cornell University Disseration (Aug. 1, 2007).

Siddiqi et al., "Medial Representation: Mathematics, Alogrithms and Applications," Kluwer Academic (2007).

Communication of European Publication No. and Information on the Application of Article 67(3) EPC for European Patent Application No. 08840167.4 (Jun. 30, 2010).

Anastasiadis et al., "MRI-Guided Biopsy of the Prostate Increases Diagnostic Performance in Men with Elevated or Increased PSA Levels after Previous Negative TRUS Biopsies," Eur Urol 50(4), p. 738-749 (2006).

Bayes, "An Essay Toward Solving a Problem in the Doctrine of Chances," Philosophical Trans Royal Soc London 53, pp. 370-418 (1764).

Blum, "A transformation for extracting new descriptors of shape" In W. Wathen-Dunn (Ed.) Models for the Perception of Speech and Visual Form. MIT Press, Cambridge MA, pp. 363-380 (1967).

Bookstein, "Principal warps: Thin-plate splines and the decomposition of deformations," IEEE Transactions on Pattern Analysis and Machine Intelligence 1, No. 6 (1989).

Borboroglu et al., "Extensive Repeat Transrectal Ultrasound Guided Prostate Biopsy in Patients with Previous Benign Sextant Biopsies," J Urol, 163(1) pp. 158-162 (Jan. 2000).

Brechbuhler et al., "Parameterization of closed surfaces for 3-D shape description," Computer Vision, Graphics, and Image Processing: Image Understanding 61, pp. 195-170 (1995).

Broadhurst, "Statistical Estimation of Histogram Variation for Texture Classification, in Texture," In conjunction with International Conference on Computer Vision (ICCV: 25-30 (2005).

Broadhurst et al., "A Statistical Appearance Model Based on Intensity Quantiles," Proc IEEE International Symposium on Biomedical Imaging (ISBI), 422-425 (2006).

Brock et al., "Inclusion of organ deformation in dose calculations," Med Phys, 30(3), pp. 290-295 (Mar. 2003).

Brock et al., "Technical note: creating a four-dimensional model of the liver using finite element analysis," Med Phys. 29(7), pp. 1403-1405 (Jul. 2002).

Casciani et al., "Prostate Cancer: value of magnetic resonance spectroscopy 3D chemical shift imaging," Abdominal Imaging 31 pp. 490-499 (2006).

Catalona at al., "Comparison of percent free PSA, PSA density, and age-specific PSA cutoffs for prostate cancer detection and staging," J Urol 56(2), pp. 255-260 (2000).

Cates et al., "Shape modeling and analysis with entropy-based particle systems," Inf Process Med Imaging 20, pp. 333-345 (2007).

Catmull, "Recursively generated b-spline surfaces on arbitrary topological meshes," Computer Aided Design 10, pp. 183-188 (1978).

Chaney et al., "Automatic male pelvis segmentation from CT images via statistically trained multi-object deformable m-rep models," Presented at American Society for Therapeutic Radiology and Oncology (ASTRO) (2004).

Christensen et al., "3D Brain mapping using a deformable neuroanatomy," Phys Med Biol 39, pp. 609-618 (1994).

Claus et al., "Pretreatment evaluation of prostate cancer: Role of MR imaging and 1H MR spectroscopy," Radiograhics 24(suppl 1) pp. S167-S180 (2004).

Cootes et al., "Active shape models—their training and application," Computer Vision, Grapics, Image Processing: Image Understanding 1, pp. 38-59 (1994).

Cootes et al., "The use of active shape models for locating structures in medical images," Image and Vision Computing, vol. 12, No. 6, pp. 335-366 (1994).

Crouch et al., "Medially Based with Finite Element Analysis of Prostate Deformation.: Medical Image Computing and Computing-Assisted Intervention," Proceedings, Part I, Randy E. Ellis, Terry M. Peters (Eds.) 108-115, Springer, NY. (2003).

Crouch et al., "Automated Finite Element Analysis for Deformable Registration of Prostate Images," IEEE Trans Med Imaging (2007).

Danielsson, "Euclidean distance mapping," Computer Graphics and Image Processing, pp. 227-248 (1980).

Delingette et al., "Topology and Shape Constraints on Parametric Active Contours," Computer Vision and Image Understanding, vol. 83, No. 2, pp. 140-171(32) (Sep. 2001).

Denberg et al., "Patient treatment preferences in localized prostate carcinoma: The influence of emotion, misconception, and anecdote," Cancer 107(3), pp. 620-630 (2006).

DiMaio et al., "A System for MRI-guided Prostate Interventions," Proc Int Conf Biomedical Robotics and Biomechatronics (2006).

Eskew et al., "Systematic 5 region prostate biopsy is superior to sextant method for diagnosing carcinoma of the prostate," J Urol 157(1), pp. 199-202 (Jan. 1997).

Flanigan et al., "Accuracy of digital rectal examination and transrectal ultrasonography in localizing prostate cancer," J Urol 152(5 Pt 1), pp. 1506-1509 (Nov. 1994).

Fletcher et al., "Principal Geodesic Analysis on Symmetric Spaces: Statistics of Diffusion Tensors," Lecture Notes in Computer Science, Springer-Verlag, vol. 3117, pp. 87-98 (2004).

Fletcher et al., "Principal geodesic analysis for the study of nonlinear statistics of shape," IEEE Transactions on Medical Imaging 23, pp. 995-1005 (2004).

Foskey et al., "A Software Toolkit for Multi-Image Registration and Segmentation IGRT and ART," Phys. 34, p. 2351 (2007).

Foskey et al., "Large deformation 3D image registration in image-guided radiation therapy," Phys Med Biol, 50, pp. 5869-5892 (2005).

Frauscher et al., "Comparison of contrast enhanced color Doppler targeted biopsy with conventional systematic biopsy: impact on prostate cancer detection," J Urol 167(4), pp. 1648-1652 (2002).

Freedman et al., "Model-based segmentation of medical imagery by matching distributions," IEEE TMI 24(3), pp. 281-292 (2005).

Fütterer et al., "Initial experience of 3 Tesla endorectal coil magnetic resonance imaging and 1H-Spectroscopic imaging of the prostate," Invest Radiol 39(11), pp. 671-680 (2004).

Fütterer et al., "Prostate Cancer: Local staging at 3-T endorectal MR imaging," Radiology 238(1), pp. 184-191 (2006).

Gee et al., "Elastically deforming 3D atlas to match anatomical brain images," J Comput Assist Tomogr 17(2), pp. 225-236 (1993).

Grimson et al., "Image-guided surgery," Sci Am., 280(6), pp. 62-69 (Jun. 1999).

Han et al., "Geometrically proper models in statistical training," Presented at Information Processing in Medical Imaging (IPMI), Nico Karssemeijer and Boudewijn Lelieveldt, eds. (2007).

Han et al., "Multi-figure anatomical objects for shape statistics," Presented at Information Processing in Medical Imaging (IPMI) (2005).

Harden et al., "Quantitative GSTP1 methylation and the detection of prostate adenocarcinoma in sextant biopsies," J Natl Cancer Inst 95(21), pp. 1634-1637 (Nov. 5, 2003).

Haris et al., "Model-Based Morphological Segmentation and Labeling of Coronary Angiograms," IEEE Trans Med Imaging, Special Issue on Model-Based Analysis of Medical Images,18(10), pp. 1003-1015 (Oct. 1999).

Hawkes et al., "Tissue deformation and shape models in image-guided interventions: a discussion paper," Med Image Anal. 9(2), pp. 163-175 (Apr. 2005).

Zeng et al., "Segmentation and Measurement of the Cortex from 3D MR Images Using Coupled Surfaces Propagation," EEE Trans Med Imaging, Special Issue on Model-Based Analyis of Medical Images, 18(10) (Oct. 1999).

Pizer et al., "Deformable M-Reps for 3D Medical Image Segmentation," Int J Comp Vision 55(2/3) (2003).

Jemal et al., "Cancer Statistics," CA Cancer J Clin 2005 55, pp. 10-30 (2005).

(56) References Cited

OTHER PUBLICATIONS

Jones et al., "Segmentation using models with affinity-based localization," In: Lecture Notes in Computer Sciences, 1205, pp. 53-62, Springer (1997).
Joshi et al., "Unbiased diffeomorphic atlas construction for computational anatomy," Neuroimage, 23 Suppl 1, pp. S151-S160 (2004).
Kaji et al., "Proton two-dimensional chemical shift imaging for evaluation of prostate cancer: External surface coil vs. endorectal surface coil," J Magn Reson Imaging 16, pp. 697-706 (2002).
Kaplan et al., "Real-time MRI-ultrasound image guided stereotactic prostate biopsy," Magn Reson Imaging 20, pp. 295-229 (2002).
Kass et al., "Snakes: Active Contour Models," Int J Comp Vision 1, pp. 321-331 (1987).
Kelemen et al., "Three-dimensional model-based segmentation," IEEE-TMI, 18(10), pp. 828-839 (1999).
Kelemen et al., "Elastic model-based segmentation of 3-D neuroradiological data sets," Medical Imaging, IEEE Transactions on, vol. 18, No. 10, pp. 828-839 (Oct. 1999).
Klinder et al., "Automated Model-Based Rib Cage Segmentation and Labeling in CT Images," Medical Image Computing and Computer-Assisted Intervention (MICCAI) pp. 195-202 (2007).
Kumar et al., "Transrectal ultrasound-guided biopsy of prostate voxels identified as suspicious of malignancy on three-dimensional (1)H MR spectroscopic imaging in patients with abnormal digital rectal examination or raised prostate specific antigen level of 4-10 ng/ml," NMR Biomed (Aug. 8, 2006).
Kurhanewicz et al., "Combined magnetic resonance imaging and spectroscopic imaging approach to molecular imaging of prostate cancer," J Magn Reson Imaging 16, pp. 451-463 (2002).
Kurhanewicz et al., "Three dimensional H-1 MR spectroscopic imaging of the in situ human prostate with high (0.24-0.7 cm3) spatial resolution," Radiology 198, pp. 795-805 (1996).
Lee et al., "Bioimpedance: novel use of a minimally invasive technique for cancer localization in the intact prostate," Prostate 39(3), pp. 213-218 (1999).
Levy et al., "Prostate and Bladder Segmentation Using a Statistically Trainable Model," American Society for Therapeutic Radiology and Oncology (ASTRO), Oct. 2007. International Journal of Radiation Oncology,Biology,Physics , vol. 69 Issue 3 , pp. S353-S353 (Oct. 2007).
Levy et al., "Multiscale Alignement of Bladder Models Towards Clinically Realistic Cross-Patient Segmentation." SAMSI Program on Geometry and Statistics of Shape Spaces, (Jul. 2007).
Liu et al., "A Large-to-Fine Shape Prior for Probabilistic Segmentations Using A Deformable M-rep". To Appear, IEEE CVPR Workshop on Mathematical Methods in Biomedical Image Analysis (MMBIA) (2008).
Lu et al., "Fast free-form deformable registration via calculus of variations," Phys Med Biol 49, pp. 3067-3087 (2004).
Maintz et al., "A survey of medical image registration," Med Image Anal 2(1), pp. 1-36 (1998).
Marsland et al., "Constructing diffeomorphic representations for the groupwise analysis of nonrigid registrations of medical images," IEEE Trans Med Imaging. 23(8), pp. 1006-1020 (Aug. 2004).
Merck et al., "Training models of anatomic shape variability," Medical Physics. pp. 1-31 (2007).
McInerney et al., "Topology Adaptive Deformable Surfaces for Medical Image Volume Segmentation," IEEE Trans Med Imaging, Special Issue on Model-Based Analysis of Medical Images, 18(10), pp. 840-850 (Oct. 1999).
McInerny et al., "Deformable models in medical image analysis: a survey," Medical Image Analysis 1(2) pp. 91-108 (1996).
McInerney et al., "Deformable Models in Medical Image Analysis," Proceedings of the Workshop on Mathematical Methods in Biomedical Image Analysis, Cat. # 96TB100056, Institue of Electrical and Electronics Engineers (IEEE), Los Alamitos, CA, pp. 171-180 (1996).
Miller et al., "Incidence of initial local therapy Natl among men with lower-risk prostate cancer in the United States," J Natl Cancer Inst. 98(16), pp. 1134-1141 (2006).

Mohan et al., "Use of deformed intensity distributions for on-line modification of image-guided IMRT to account for interfractional anatomic changes," Int J Rad Oncol Biol Phys 61(4), pp. 1258-1266 (2005).
Montagnat et al., "Volumetric medical images segmentation using shape constrained deformable models," In: Lecture Notes in Computer Sciences, 1205, pp. 13-22, Springer (1997).
Muller et al., "Limitations of High Dimension, Low Sample Size Principal Components for Gaussian Data," (Feb. 2008).
Noble, "Ultrasound Image Segmentation: A Survey," IEEE TMI 25(8), pp. 987-1010 (Aug. 2006).
Noguchi et al., "Relationship between systematic biopsies and histological features of 222 radical prostatectomy specimens: lack of prediction of tumor significance for men with nonpalpable prostate cancer," J Urol 166(1), pp. 104-109 (Jul. 2001).
Pekar et al., "Automated model-based organ delineation for radiotherapy planning in prostatic region," Int J Rad Oncol Biol Phys 60, pp. 973-980 (2004).
Pelzer et al., "Prostate cancer detection in men with prostate specific antigen 4 to 10 ng/ml using a combined approach of contrast enhanced color Doppler targeted and systematic biopsy," J Urol 173(6), pp. 1926-1929 (2005).
Philip et al., "Importance of peripheral biopsies in maximising the detection of early prostate cancer in repeat 12-core biopsy protocols," BJU Int 98(3), pp. 559-562 (Mar. 31, 2006).
Pinkstaff et al., "Systematic transperineal ultrasound-guided template biopsy of the prostate: three-year experience," Urology 65, pp. 735-739 (2005).
Pizer et al., "Deformable m-reps for 3D medical image segmentation," Int J Comp Vision, 55, pp. 85-106 (2003).
Pizer et al., "A Method and Software for Segmentation of Anatomic Object Ensembles by Deformable M-Reps," Med Phys 32(5), pp. 1335-1345 (2005).
Pizer et al., "Intra-Patient Anatomic Statistical Models for Adaptive Radiotherapy," in to appear in MICCAI Workshop From Statistical Atlases to Personalized Models: Understanding Complex Diseases in Populations and Individuals (Oct. 2006).
Pizer et al., "Segmentation by Posterior Optimization of M-reps: Strategy and Results," Submitted for journal review (2007).
Pizer et al., "Synthesis, Deformation, and Statistics of 3D Objects via M-reps in Medial Representations: Mathematics, Algorithms and Applications," Siddiqi, K., Pizer, S., eds. (2007).
Prando et al., "Prostatic biopsy directed with endorectal MR spectroscopic imaging findings in patients with elevated prostate specific antigen levels and prior negative biopsy findings: early experience," Radiology 236(3), pp. 903-910 (2005).
Provencher, "Automatic quantitation of localized in vivo 1H spectra with LC Model," NMR Biomed 14, pp. 260-264 (2001).
Rabbani et al., "Incidence and clinical significance of false-negative sextant prostate biopsies," J Urol 159(4), pp. 1247-1250 (Apr. 1998).
Rao et al., "Comparison of Human and Automatic Segmentations of Kidneys from CT Images," Int J Rad Oncol Bio Phys 61(3), pp. 954-960 (2005).
Rasch et al., "Definition of the prostate in CT and MRI: A multiobserver study," Int J Radiat Oncol Biol Phys 43, pp. 57-66 (1999).
Rosen et al., "3T MR of the prostate: Reducing susceptibility gradients by inflating the endorectal coil with a barium sulfate suspension," Mag Reson Med, 57, pp. 898-904 (2007).
Scheidler et al., "Prostate cancer: Localization with three-dimensional proton spectroscopic imaging—Clinicopathologic Study," Radiology 213, pp. 473-480 (1999).
Shen et al., "Optimized prostate biopsy via statistical atlas of cancer spatial distribution," Medical Image Analysis 8, pp. 139-150 (2004).
Smith et al., "Prostate volume contouring: A 3D analysis of segmentation using 3DTRUS, CT, and MR," Int J Rad Oncol Biol Phys 67(4), pp. 1238-1247 (2007).
Sohn et al., "Modelling individual geometric variation based on dominant eigenmodes of organ deformation: implementation and evaluation," Physics in Medicine and Biology, vol. 50 (2005).
Styner et al., "Statistics of Pose and Shape in Multiobject Complexes Using Principal Geodesic Analysis," Medical Imaging and Augmented Reality, LNCS 4091, pp. 1-8 (2006).

(56) References Cited

OTHER PUBLICATIONS

Swindle et al., "Pathologic characterization of human prostate tissue with proton spectroscopy," Radiology 228, pp. 144-151 (2003).
Thirion, "Image matching as a diffusion process: an analogy with Maxwell's demons," Medical Image Analysis vol. 2, Issue 3, pp. 243-260 (Sep. 1998).
Varma et al., "Classifying images of materials: achieving viewpoint and illumination independence," Proc ECCV 2002, Lecture Notes in Computer Science 2352, p. 255 (2002).
Vehkomäki et al., "User-guided tool for efficient segmentation of medical image data," In: Lecture Notes in Computer Sciences, 1205, pp. 685-694, Springer (1997).
Wang et al., "Implementation and validation of a three-dimensional deformable registration algorithm for targeted prostate cancer radiotherapy," Int J Rad Oncol Biol Phys 61, pp. 725-735 (2005).
Warfield et al., "Simultaneous truth and performance level estimation (STAPLE): an algorithm for the validation of image segmentation," IEEE Trans on Med Imaging, 23:7, pp. 903-921 (2004).
Wefer et al., "Sextant localization of prostate cancer: Comparison of sextant biopsy, magnetic resonance imaging and magnetic resonance spectroscopic imaging with step section histology," J Urol 164, pp. 400-404 (Aug. 2000).
Wong et al., "Image-guided radiotherapy for prostate cancer by CT-linear accelerator combination prostate movements and dosimetric considerations," Int J Radiat Oncol Biol Phys 61, pp. 561-569 (2005).
Yan et al., "An off-line strategy for constructing a patient-specific planning target volume in adaptive treatment process for prostate cancer," Int J Radiat Oncol Biol 48(1), pp. 289-302 (2000).
Yan et al., "A model to accumulate fractionated dose in a deforming organ," Int J Radiat Oncol Biol Phys. 44(3), pp. 665-675 (Jun. 1, 1999).
Yuen et al., "Endorectal magnetic resonance imaging and spectroscopy for the detection of tumor foci in men with prior negative transrectal ultrasound prostate biopsy," J Urol 171(4), pp. 1482-1486 (Apr. 2004).
Zakian et al., "Correlation of proton MR spectroscopic imaging with Gleason score based on step-section pathologic analysis after radical prostatectomy," Radiology 234, pp. 804-814 (2005).
Zhan et al., "Deformable segmentation of 3-D ultrasound prostate images using statistical texture matching method," IEEE Transactions on Medical Imaging 25(3), pp. 256-272 (2006).
Zhan et al., "Targeted Prostate Biopsy Using Statistical Image Analysis," IEEE Transactions On Medical Imaging 26(6), pp. 779-788 (2007).
International Search Report for International Application No. PCT/US2008/080504 (May 29, 2009).
Second Office Action for Japanese Patent Application No. 2010-530175 (May 15, 2013).
Office Action for Japanese Patent Application No. 2010-530175 (Nov. 5, 2012).
Notice of Allowance and Fee(s) Due for U.S. Appl. No. 08/885,330 (Dec. 7, 1998).
Balter, et al., "Correlation of projection radiographs in radiation therapy using open curve segments and points," Med Phys., vol. 19 (2), pp. 329-334 (Mar./Apr. 1992).
Balter, "Registration of radiographs in radiation therapy using open curve segments: Method and applications," Doctoral dissertation, University of Chicago, pp. 1-144 (1992).
Blackall et al., "Alignment of Sparse Freehand 3D Ultrasound with Preoperative Images of the Liver Using Models of Respoitory Motion and Deformation," IEEE Transactions on Medical Imaging, vol. 24, No. 11, pp. 1405-1416 (Nov. 2005).
Blum et al., "Shape Description Using Weighted Symmetric Axis Features," Pattern Recognition, vol. 10, pp. 167-180 (1978).
Borgefors, "Hierarchical Chamfer Matching: A Parametric Edge Matching Algorithm," IEEE Trans PAMI, vol. 10, No. 6, pp. 849-865 (1988).
Borgefors, "An Improved Version of the Chamfer Matching Algorithm," Proc. 7th Intl. Conf. Pattern Recognition, pp. 1175-1177 (1984).
Boyer, et al., "A review of electronic portal imaging devices (EPIDs)," Med Phys., vol. 19 (1), pp. 1-16 (Jan./Feb. 1992).
Burbeck et al., "Linking Object Boundaries at Scale: a Common Mechanism for Size and Shape Judgments," Vision Research, vol. 36, No. 3, pp. 361-372 (1996).
Burbeck et al., "Object Representation by Cores: Identifying and Representing Primitive Spatial Regions," Vision Research, vol. 35, No. 13, pp. 1917-1930 (1995).
Chakraborty et al., "Deformable Boundary Finding Influenced by Region Homogeneity," Proc. Conf. Computer Vision and Pattern Recognition (CVPR), pp. 624-627 (1994).
Dongola et al., "How I do it: Ultrasound-guided transrectal biopsy of the prostate," CME Radiology, 2(3), pp. 134-138 (2001).
Eberly et al., "Ridges for Image Analysis," Journal of Mathematical Imaging and Vision, vol. 4, pp. 351-371 (1994).
Eberly et al., "A Differential Geometric Approach to Anisotropic Diffusion," Geometry-Driven Diffusion in Computer Vision, pp. 371-392 (1994).
Fritsch et al., "Localization and Segmentation of Medical Image Objects Using Deformable Shape Loci," Inf. Processing in Med. Imaging (IPMI), Lecture Notes in Computer Science, pp. 127-140 (1997).
Fritsch et al., "Core Based Portal Image Registration for Automatic Radiotherapy Treatment Verification," Int. Jnl. Radiat. ONcol. Biol. Phys., 33(5), pp. 1287-1300 (1995).
Fritsch et al., "The Multiscale Medial Axis and its Applications in Image Registration," Pattern Recognition Letters, vol. 15, pp. 445-452 (May 1994).
Fritsch et al., "Cores for Image Registration," Medical Imaging; Image Processing, SPIE Proceedings, vol. 2167, pp. 128-142 (1994).
Fritsch et al., "Stimulated Cores and their Applications in Medical Imaging," University of North Carolina at Chapel Hill Department of Radiation Oncology technical report. To appear as poster in Information Processing in Medical Imaging 1995 (IPMI '95) (1994).
Fritsch, "Registration of Radiotherapy Images Using Multiscale Medial Descriptions of Image Structure," Ph.D. Dissertation, Department of Biomedical Engineering, The University of North Carolina at Chapel Hill, pp. 1-137 (Part 1 of 2) (1993).
Fritsch, "Registration of Radiotherapy Images Using Multiscale Medial Descriptions of Image Structure," Ph.D. Dissertation, Department of Biomedical Engineering, The University of North Carolina at Chapel Hill, pp. 138-309 (Part 2 of 2) (1993).
Frome, "Psychophysical Study of Shape Alignment," Technical Report TR-198, Computer Science Center, University of Maryland, pp. 1a-42 (1972).
Gilhuijs, et al., "Automatic on-line inspection of patient setup in radiation therapy using digital portal images," Med Phys., vol. 20, No. 3, pp. 667-677 (May/Jun. 1993).
Han et al., "Interpolation in Discrete Single Figure Medial Objects," IEEE Computer Society Workshop on Mathematical Methods in Biomedical Image Analysis (MMBIA), pp. 1-8 (2006).
Horn et al., "Determining Optical Flow," Artificial Intelligence Laboratory, Massachusetts Institute of Technology, Cambridge, MA, pp. 185-203 (1998).
Hu, "Visual Pattern Recognition by Moment Invariants," IRE Trans. Info. Theory, vol. 8, No. 2, pp. 179-187 (1962).
Johnson et al., "Analysis and Reconstruction of Medical Images Using Prior Information, with Discussion," Case studies in Applied Bayesian Statistics II, pp. 149-238 (1995).
Leymarie et al., "Tracking Deformable Objects in the Plane Using an Active Contour Model," IEEE Trans PAMI, vol. 15, No. 6, pp. 617-634 (1993).
Lindeberg, "Scale-Space Theory in Computer Vision," Kluwer Academic Publishers, pp. 149-162 (1994).
Lindeberg et al., "Ch. 1: Linear scale space I: Basic Theory and Ch. 2: Linear scale space II: Early Visual Operations," Geometry-Driven Diffusion in Computer Vision, Kluwer Academic Publishers, Dordrecht, pp. 1-72 (1994).
Liu et al., "Volume registration using the 3D core," Proceedings of Visualization in Biomedical Computing, SPIE Proc. vol. 2359, pp. 217-226 (1994).
McAuliffe et al., "Scale-Space Boundary Evolution Initialized by Cores," Proceedings of the Fourth Intl. Conf. on Visualization in

(56) References Cited

OTHER PUBLICATIONS

BioMed. Computing, Hamburg, IEEE Computer Society Press, Los Alamitos, CA, pp. 173-183 (1996).

McInerney et al., "Medical Image Segmentation Using Topologically Adaptable Surfaces," Lecture Notes in Compo Sci. #1205, J. Trocca, et al. Proc. CVRMED-MRCAS '97, Springer, pp. 23-32 (1997).

Morse et al., "Zoom-Invariant Vision of Figural Shape: Effects on cores of Image Disturbances," UNC Tech Report, TR 96-005 (Mar. 1996).

Morse et al. "General shape and specific detail: Context-dependent use of scale in determining visual form," Proc. 2nd International Workshop on Visual Form, pp. 374-383, World Scientific, Singapore (1994).

Morse et al., "Multiscale medial analysis of medical images," Image & Vision Computing, vol. 12, pp. 327-338 (Jul./Aug. 1994).

Pilgram et al., "Common shape model and inter-individual variations of the heart using medial representation: a pilot study," Technical report, Institute for Medical Knowledge Representation and Visualization, University for Health Informatics and Technology, Tyrol, Austria, pp. 1-30 (2003).

Pizer et al., "Zoom-invariant Vision of Figural Shape: The Mathematics of Cores," UNC Computer Sci Tech Report, TRN 96-004, pp. 1-43 (1996).

Pizer et al., "Segmentation, registration, and measurement of shape variation via image object shape," IEEE Transactions on Medical Imaging, 18(10), pp. 851-865 (1997).

Pizer et al., "3D Image-guided surgery via registration of intraoperative and preoperative images." Proc. Conf. on Interactive Technology in Surgery and Medicine, Leeds, UK (1995).

Pizer et al., "Object shape before boundary shape: scale-space medial axes. Presented at Shape in Picture, (NATO Advanced Research Workshop)," Journal of Mathematical Imaging and Vision, vol. 4, pp. 303-313 (1994).

Pizer et al., "Objects, Boundaries, and Medical Image Analysis," University of North Carolina Computer Science Department technical report TR94-069 (1994).

Pizer et al., "Core-based boundary claiming," Medical Imaging '94: Image Processing, SPIE 2167:151-159 (1994).

Pizer et al., "Human perception and computer image analysis of objects in images," Proc. Conference of the Australia Pattern Recognition Society (DICTA), I, pp. 19-26 (1993).

Press, et al., "Numerical Recipes: The Art of Scientific Computing; Section 17.2—Diffusive Initial Value Problems," Cambridge University Press, Cambridge, MA, pp. 635-642 (1986).

Psotka, "Perceptual Processes That May Create Stick Figures and Balance", Journal of Experimental Psychology: Human Perception and Performance, vol. 4, No. 1, pp. 101-111 (1978).

Radeva et al., "A Snake for Model-Based Segmentation," IEEE Trans PAMI 8, pp. 816-821 (1995).

Sherouse et al., "The Portable Virtual-Simulator," Int. J. Radiation Oncology Bioi. Phys., vol. 21, pp. 475-482 (1991).

Sherouse et al., "Computation of Digitally Reconstructed Radiographs for Use in Radiotherapy Treatment Design," in J. Radiat. Oncol. Bioi. Phys, vol. 18, pp. 651-658 (1990).

Staib et al., "Model-Based Deformable Surface Finding for Medical Images," IEEE Trans. Med. Imag., vol. 15, No. 5, pp. 720-731 (Oct. 1996).

Szekely et al., "Segmentation of 2-D and 3-D objects from MRI volume data using constrained elastic deformation of flexible Fourier contour and surface models," Medical Image Analysis, vol. 1, No. 1, pp. 19-34, Oxford University Press (1996).

Vaillant, et al., "Using Extremal Boundaries for 3-D Object Modeling," IEEE Transactions on Pattern Analysis and Machine Intelligence vol. 14, No. 2, pp. 157-173 (Feb. 1992).

van den Eisen, et al., "Medical Image Matching—A Review with Classification," IEEE Eng. Med. Biology, vol. 12:1, pp. 26-39 (Mar. 1993).

Wilson et al., "Towards a Framework for Automated Image Analysis, Image Fusion and Shape Variability Techniques," Proc. 16th Leeds Annual Statistical Research Workshop, University of Leeds Press, pp. 13-20 (1996).

Wilson, "Statistical Models for Shapes and Deformations," Ph.D. Dissertation, Institute of Statistics and Decision Sciences, Duke University, pp. 1-127 (1995).

\* cited by examiner

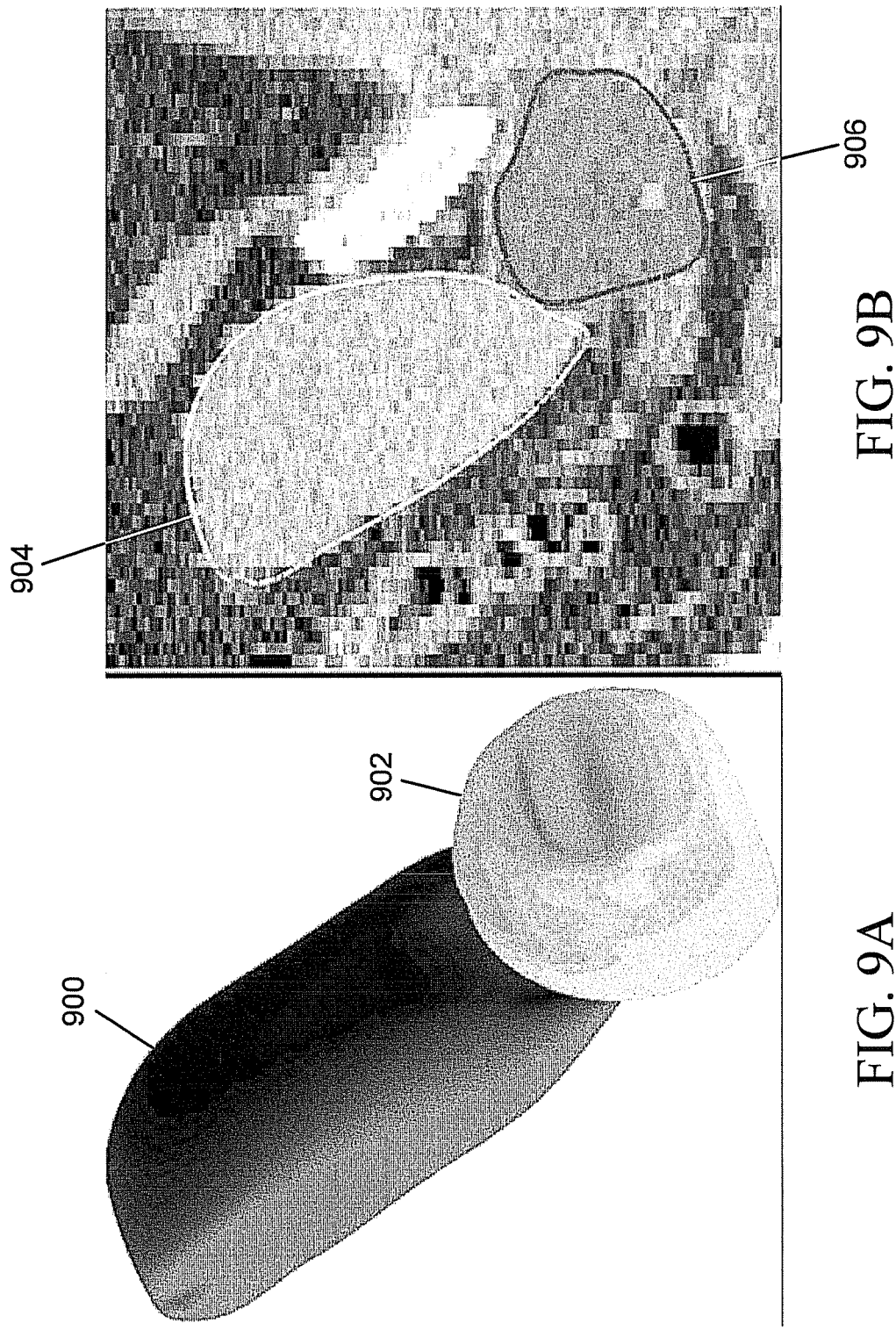

METHODS, SYSTEMS, AND COMPUTER READABLE MEDIA FOR MAPPING REGIONS IN A MODEL OF AN OBJECT COMPRISING AN ANATOMICAL STRUCTURE FROM ONE IMAGE DATA SET TO IMAGES USED IN A DIAGNOSTIC OR THERAPEUTIC INTERVENTION

RELATED APPLICATIONS

This application claims the benefit of U.S. Provisional Patent Application Ser. No. 60/999,420 filed Oct. 18, 2007 and U.S. Provisional Patent Application Ser. No. 61/087,026 filed Aug. 7, 2008; the disclosures of which are incorporated herein by reference in their entireties.

GRANT STATEMENT

Some of the work involved in creating this invention was supported by NCI and NIBIB Grant Number P01 EB002779. Thus, the U.S. Government has certain rights to this invention.

TECHNICAL FIELD

The subject matter described herein relates to medical image segmentation and analysis. More specifically, the subject matter relates to methods, systems, and computer readable media for mapping regions in a model of an object comprising an anatomical structure from one image data set to images used in a diagnostic or therapeutic intervention.

BACKGROUND

Prostate cancer (CaP) is a major health issue in the United States, with 240,000 diagnoses and 30,000 deaths in 2005. CaP accounts for 33% of all new incidences of non-skin cancer in the United States male population, by far the greatest rate among all non-skin cancers, and the annual death rate is second only to lung/bronchial cancer. Due to the prevalence and serious consequences of CaP, 1.3-1.5 million patients in the United States annually undergo transrectal ultrasound imaging (TRUS)-guided interventional prostate procedures, with biopsy being the most common. Other procedures include insertion of radioactive seeds (brachytherapy) and tissue ablation by methods that freeze or heat tissue.

During biopsy, small-gauge hollow needles are introduced into the prostate to collect core tissue samples under visual guidance of TRUS. While TRUS reveals the overall shape of the prostate well, a major disadvantage is the inability to differentiate between normal and cancerous tissues inside the prostate. Due to this limitation, tissue samples are collected based on a pre-defined grid pattern applied to all patients. Unfortunately the false negative rate of this approach is high (~25-30%). Moreover, even when a biopsy is positive, the tumor may be sampled incompletely, leading to an erroneously low Gleason score (tumor grade), and perhaps to inappropriate treatment decisions. Consequences of false negatives include multiple repeat biopsies over a number of years, missed cancers that continue to grow and possibly metastasize, and patient anxiety. These undesired outcomes significantly affect the patient's quality of life and contribute to health care burden and costs.

TRUS-guided biopsies suffer problems of not allowing doctors accurately enough to preferentially take biopsy samples from tissues inside the prostate that are suspicious for cancer. To overcome these problems, image segmentation may be used to identify anatomical objects of interest and intervention-target regions within them such as potentially cancerous portions of the anatomical structure. As used herein, "image segmentation" refers to the process of partitioning a digital image into a region (i.e., sets of voxels or pixels) in order to find anatomic entities relevant to the medical procedure. Image segmentation may be used to locate objects and boundaries (lines, curves, etc.) appearing in various types of medical images including, but not limited to, magnetic resonance images (MRI) and computed tomography (CT) images.

Thus, segmenting an image divides the image into various regions, wherein voxels in positions inside and outside the object region, or regions, are similar at corresponding positions to an atlas (i.e., a template image, possibly equipped with information as to its variation across cases), with respect to some characteristic or property, such as color, intensity, or texture. In addition to using appearance information in image segmentation, model-based segmentation assumes that objects of interest (i.e., organs, tumors, etc.) have a repetitive geometry and, therefore, a model of the object can be created and used to impose probabilistic constraints on the segmentation of the image, thereby increasing its accuracy.

Two examples of images that may be used to perform image segmentation for medical purposes, including CaP screening and treatment, are a magnetic resonance image (MRI) and an ultrasound (US) image. From such an image one may extract a geometric model of an anatomical structure within a patient that may be used to help make critical treatment planning and delivery decisions, such as aiming a needle for biopsy or for inserting radioactive seeds for treatment. However, current methods for extracting an object model from ultrasound images used to guide clinical procedures, and even extraction from images such as MRI used to plan procedures, require expert human interaction and thus are extremely time consuming and expensive. Moreover humans, even experts with similar training, are known to exhibit inter- and intra-user variabilities that can adversely affect clinical decisions.

Some images used for planning an intervention, such as biopsy, contain not only information about the object of interest, such as a prostate, but also information about where an intervention target region within it is situated. Alternatively, it may be possible to acquire a separate image perfectly registered with the image showing the object of interest, and showing the location of the intervention. Recent research has demonstrated that magnetic resonance spectroscopy images (MRSI) acquired simultaneously and in full registration with MR images may yield high sensitivity for detecting regions within the prostate that are suspicious for CaP, i.e., a target region for the intervention.

Unfortunately it is impractical to routinely perform biopsy and therapeutic procedures under direct visual guidance of images showing degree of suspicion for cancer because the guidance requires real time imaging techniques, such as TRUS, that show the anatomic object but give no information as to degree of suspicion for disease.

Accordingly, in light of these difficulties, a need exists for improved methods, systems, and computer readable media for transferring intervention target regions from the images from which they are derived into the intervention-guiding image. This need is satisfied by mapping a model of an object comprising an anatomical structure, which was derived from a planning image, to the image data used to guide a diagnostic or therapeutic intervention.

SUMMARY

Methods, systems, and computer readable media for mapping a model of an object comprising an anatomical structure segmented from a planning image to an intervention-guiding image of a different type from which the object was derived, and thereby mapping a region contained in the object to the intervention-guiding image are disclosed. According to one method, an initial medial representation object model (m-rep) of an object comprising an anatomical structure is created based on image data of at least a first instance of the object. A patient-specific m-rep is created by deforming the initial m-rep based on planning-image data of at least a second instance of the object, wherein the at least a second instance of the object is associated with the patient and identifying an intervention target region registered with the planning image data. The patient-specific m-rep is correlated to the intervention-guiding image data of the at least second instance of the object, which has been deformed from its state in the planning image data. The intervention target region may then be identified by a mapping derived from a transformation between the m-rep in the planning image data and the m-rep in the intervention-guiding image data.

A system for mapping a model of an object comprising an anatomical structure to the intervention-guiding image data is also disclosed. The system includes an object model generator for generating a medial representation object model (m-rep) of an object comprising an anatomical structure based on planning image data of an object. An object model deformation and mapping module correlates then the m-rep to intervention-guiding image data of the object.

According to one aspect, the system may include probabilistic information derived from numerous instances of image data of an object type, each from a different individual (between-patient probabilistic information), as well as probabilistic information derived from numerous instances of image data of the same individual (within-patient probabilistic information). A patient-specific medial representation object model (m-rep) is based on at least a portion of the planning image data for a patient, wherein the at least a portion of the image data is associated with the object type, such as the prostate. The probabilistic information derived from other individuals is used to derive an m-rep fitted into the planning image for the patient, i.e., a patient-specific m-rep. At the time of intervention an intervention-guiding image is obtained of the same organ, and the patient-specific m-rep is deformed into the intervention-guiding image using the within-patient probabilistic information. This deformation is applied to the intervention target region within the object. A biopsy needle is guided to remove a tissue sample from the intervention target region within the object for biopsy. The guidance is provided by a display of the intervention target region overlaid on the intervention-guiding image data.

According to another aspect, deformation of the m-rep into the intervention-guiding image data of the object includes optimizing an objective function including a component relating the m-rep to the intervention-guiding image data.

As used herein, the term "object" refers to a real-world structure, such as an anatomical structure, desired to be modeled. For example, objects may include kidneys, hearts, lungs, bladders, and prostates.

The term intervention target region refers to a target for the medical intervention, such as a region marked as suspicious for some disease or as a target for treatment.

The term "object image data" refers to a set of data collected by a sensor from an object and stored on a computer. Examples of object image data include CT scan data, MRI data, x-ray data, digital photographs, or any other type of data collected from the real world that can be represented by a set of pixel intensities and positions.

As used herein, the term "medial atom" refers to a position and a collection of vectors having predetermined relationships with respect to each other and with respect to one or more medial axes in a model. Medial atoms may be grouped together to form models. For example, the medial manifold may be sampled over a spatially regular lattice, wherein elements of this lattice are called medial atoms.

The term "medial axis," as used herein, refers to a set of points equidistant from tangent points on opposite surfaces of a model and located at the intersections of orthogonal lines from the tangent points within the surfaces.

As used herein, the term "object model" refers to a mathematical representation an object including, but not limited to, its surface, interior, and shape variability.

As used herein, the term "m-rep" refers to a medial atom representation of an object or of object image data. An m-rep is an explicit mathematical representation (i.e., a model) of an object's geometry in Riemannian space that represents a geometric object as a set of connected continuous medial manifolds. For 3D objects these medial manifolds may be formed by the centers of all spheres that are interior to the object and tangent to the object's boundary at two or more points. The medial description is defined by the centers of the inscribed spheres and by the associated vectors, called spokes, from the sphere centers to the two respective tangent points on the object boundary. It is appreciated that in addition to representing the surface boundaries of objects, m-reps may also represent object interiors in terms of local position, orientation, and size and may include a single FIGURE or multiple figures. Also, an m-rep may be defined in an object based coordinate system, i.e., a coordinate system of the object of object image data being modeled.

As used herein, the term "figure" refers to a component or a sub-component of a model. Each continuous segment of a medial manifold represents a medial figure. For example, some models may have only a single FIGURE. An example of an object that can be represented by a single FIGURE is an object with a relatively simple shape, such as a kidney. An example of an object that may require multiple figures for accurate modeling is a human hand. A medial atom based model of a hand may include a main figure consisting of the palm of the hand and subfigures consisting of each finger of the hand.

As used herein, the term "voxel" refers to a volume element that represents a value on a regular grid in 3D space.

The subject matter described herein for mapping a planning image of an object comprising an anatomical structure to intervention-guiding object image data and thereby carrying an intervention-target region registered with the planning image into the intervention-guiding image may be implemented using a computer program product comprising computer executable instructions embodied in a tangible computer readable medium that are executed by a computer processor. Exemplary computer readable media suitable for implementing the subject matter described herein includes disk memory devices, programmable logic devices, and application specific integrated circuits. In one implementation, the computer readable medium may include a memory accessible by a processor. The memory may include instructions executable by the processor for implementing any of the methods for routing a call described herein. In addition, a computer readable medium that implements the subject matter described herein may be distributed across multiple physical devices and/or computing platforms.

BRIEF DESCRIPTION OF THE DRAWINGS

The subject matter described herein will now be explained with reference to the accompanying drawings of which:

FIG. 9A is a surface representation of a bladder and prostate according to an embodiment of the subject matter described herein;

FIG. 9B is a midsagittal slice of a bladder and prostate in an ultrasound scan according to an embodiment of the subject matter described herein;

DETAILED DESCRIPTION

Exemplary Operating Environment

Figure 1:
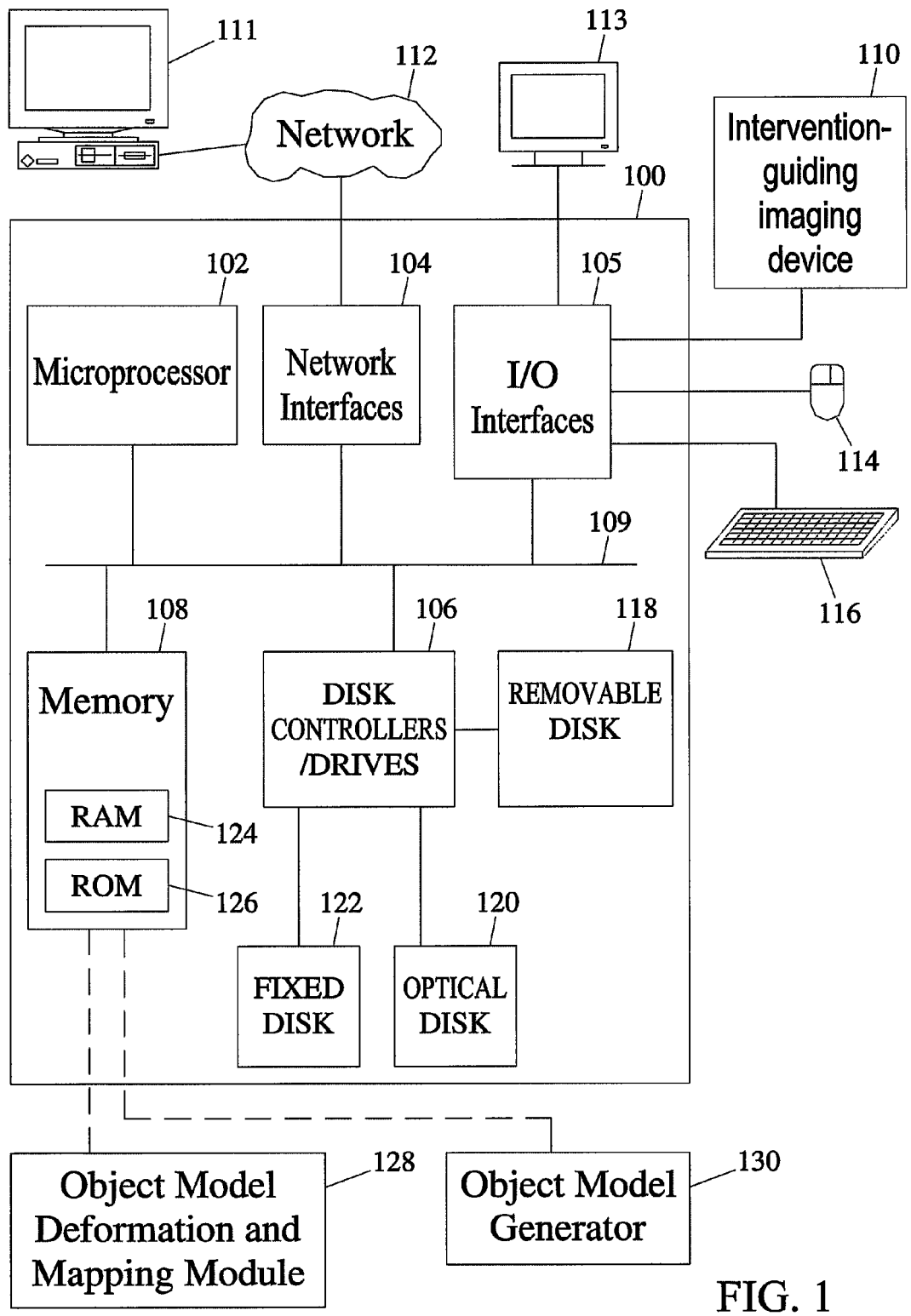
FIG. 1 is a block diagram of a general purpose computing platform on which the portion of the methods and systems bringing the model and intervention target region to the intervention-guiding image may be implemented according to an embodiment of the subject matter described herein.

The subject matter described herein includes methods and systems for mapping an object comprising an anatomical structure in a planning image and an intervention target region derived from an image registered with the planning image to intervention-guiding image data showing the object. The methods and systems of the subject matter described herein can be implemented in hardware, firmware, software, or any combination thereof. In one exemplary embodiment, the methods and systems that perform object modeling for mapping an object model comprising an anatomical structure in a planning image to an intervention-guiding image data may be implemented as application software adapted to execute on a general purpose computer. FIG. 1 illustrates an exemplary operating environment for the methods and systems for mapping the object model comprising the anatomical structure in the planning image to the intervention-guiding image data according to an embodiment of the present invention. Referring to FIG. 1, computer 100 includes a microprocessor 102, network interfaces 104, I/O interfaces 105, disk controllers/drives 106, and memory 108 connected via bus 109. Additionally, computer 100 may be connected, via I/O interfaces 105, to intervention-guiding imaging device 110 for receiving image data of, for example, an anatomical object of interest.

Microprocessor 102 may be any type of general-purpose processor suitable for executing application software. An exemplary microprocessor suitable for use with embodiments of the present invention is any of the Pentium® family of processors available from Intel® Corporation.

Network interfaces 104 may include one or more network adapter cards that communicate with one or more remote computers 111 via network 112. For example, network interfaces 104 may be Ethernet or ATM cards.

I/O interfaces 105 may provide serial ports for communicating with external devices, such as display device 113, mouse 114, and keyboard 116. I/O interfaces 105 may also include interfaces for other types of input and output devices, such as microphones and speakers.

Disk controllers/drives 106 may include hardware components for reading to and writing from storage devices, such as removable disks 118, optical disks 120, and fixed disk 122.

Memory 108 may include random access memory 124 and read only memory 126 for storing instructions to be executed by microprocessor 102. According to the present invention, memory 108 may store an instance of software 128 for deforming an object model to fit a particular instance of an object and mapping the object model to one or more ultrasound images of the object and an instance of object model generator 130 for generating a medial representation object model of an object comprising an anatomical structure based on high resolution image data of an object. Software 128 and 130 may be run on a modern PC under the Windows® operating system. Software 128 and 130 may also automatically deform medial atom models into image data and then carry the intervention target region into the intervention-guiding image. Exemplary operations that may be performed by software 128 and 130 will now be described in more detail below.

Overview

Figure 2:
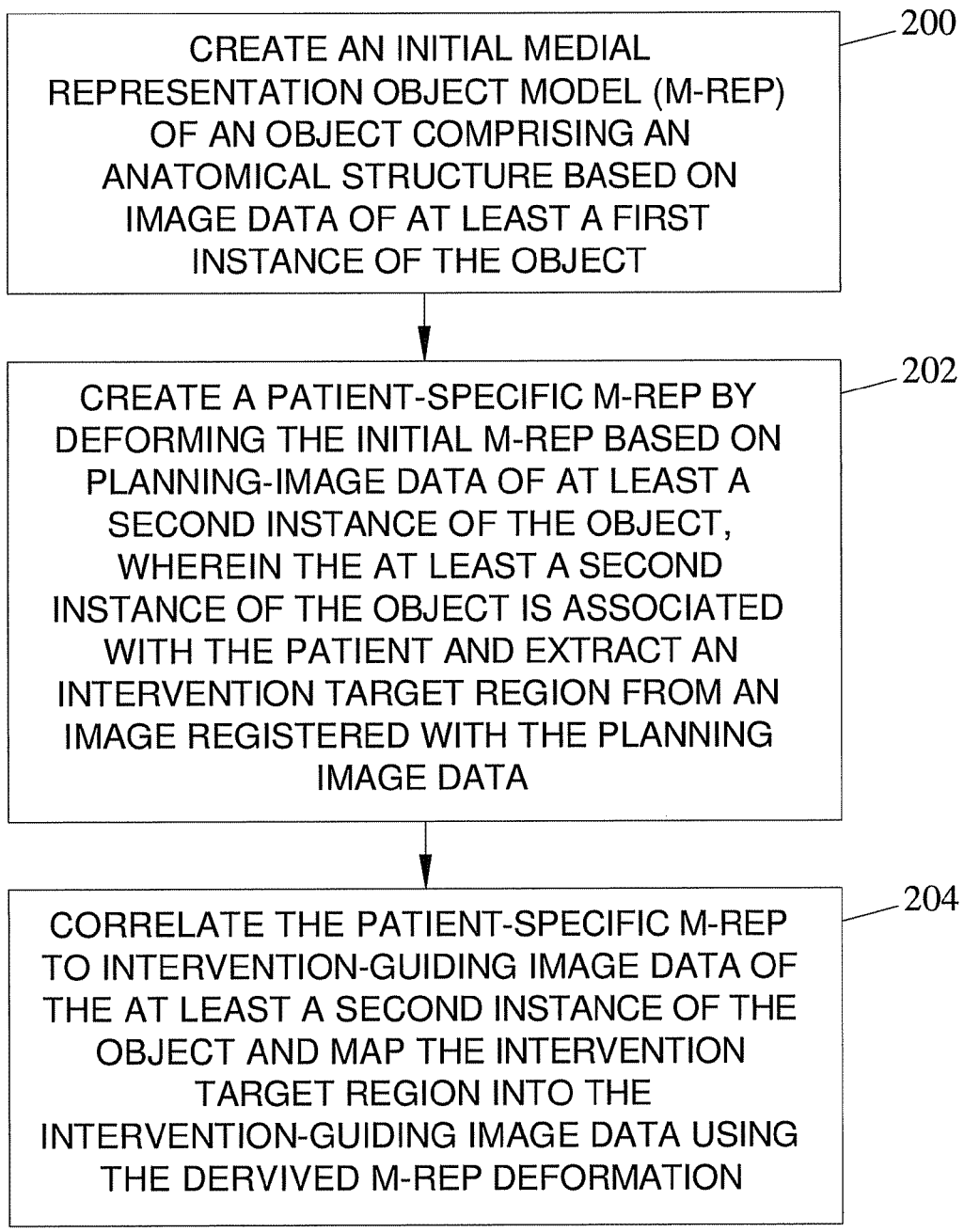
FIG. 2 is a flow chart of an exemplary process for mapping MR/MRS imaging data to a TRUS image according to an embodiment of the subject matter described herein.

According to one aspect of the subject matter described herein, object models may be automatically imbedded in a target image, rigidly registered with the corresponding target object, and then deformed to closely match the shape of the specific target object. FIG. 2 is a flow chart of an exemplary process for creating a patient-specific statistically-trainable deformable shape model of a prostate based on a planning image of the object, creating an intervention target region from an image registered with the planning image, and mapping the object model and thereby the intervention target region to a series of intervention-guiding images in order to guide a physician's biopsy needle during surgery according to an embodiment of the subject matter described herein. Referring to FIG. 2, in block 200, an initial medial representation object model (m-rep) of an object comprising an anatomical structure is created based on image data of at least a first instance of the object. The object model may initially be generic for the type of object and later customized for a specific instance of the object (i.e., patient). An m-rep may be created based on one or more pre-biopsy (e.g., MR, CT, etc.) images of an object. For example, a physician may acquire pre-biopsy MR images showing the geometric details of a prostate, including any nodules that may be present. Additionally, probability distributions of the prostate shape and the image intensity patterns in regions relative to the prostate model may be generated.

In block 202, a patient-specific m-rep is created by deforming the initial m-rep based on planning image data of at least a second instance of the object, wherein the at least second instance of the object is associated with the patient. For example, a patient-specific atlas of a prostate shape may be created by analyzing pixel intensities of the planning image, possibly in combination with using image intensity related statistical training methods. Also, an intervention target region is extracted from the planning image or another image perfectly registered with it and portraying information as to the intervention target region.

In block 204, the patient-specific m-rep is correlated to the intervention-guiding image data of the at least second instance of the object, deformed from the planning image, and the intervention target region is mapped into the intervention-guiding image data using the derived m-rep deformation. For example, the boundary/outline of the object may be accurately defined in an ultrasound image, and the intervention target region within the object, such as potentially cancerous or otherwise suspicious areas, may be carried from the planning image into the intervention-guiding image by the use of the relation between patient-specific m-rep in the planning image and the patient-specific model in the intervention-guiding image. In addition to biopsy applications (e.g., allowing physicians to plan and execute needle trajectories passing through target regions), mapping non-ultrasound images of an object to ultrasound images of the object using a deformed object model may have therapeutic and/or other diagnostic uses as well. It is appreciated that the correlation may be accomplished by an optimization process driven by probability distributions and may take into account changes in prostate shape and differences between fundamental properties of planning and intervention-guiding imaging technologies, as well as probability distributions on each, in relation to an anatomic model of the anatomic object of interest.

Additionally, the object model, as well as the intervention target region may be simultaneously displayed and overlaid onto the intervention-guiding images of the object for guiding physicians during surgical procedures. For example, during a prostate biopsy, an m-rep model and the intervention target region may be mapped to and overlaid on a TRUS image of the prostate for accurate needle placement during biopsy.

According to another aspect, the subject matter described herein includes a method based on texture analysis for the image-match term that appears in the objective function for mapping a patient-specific m-rep to TRUS images.

According to another aspect, the subject matter described herein includes a method of generating statistics on within-patient deformations between MR/MRS imaging and TRUS imaging and of representing TRUS image intensities and textures relative to a prostate/suspicion volume model to enable deformable mapping between the MR/MRS and TRUS data sets. Each of these aspects will now be described in greater detail below.

Create Initial M-rep Object Model

Image Data of an Object

As mentioned above, various types of objects may be represented in different types of digital images. These images may include planning images, such as MRI, MRSI, and CT images, or may be intervention-guiding images, such as ultrasound images (e.g., TRUS). One method for accurately identifying the boundaries of different anatomical objects represented in digital images includes manual 2D image segmentation wherein a human expert determines a boundary of an object represented in each slice of the image.

In addition to identifying the boundary of an object in a 2D image by image segmentation, a 3D model of an object may be created using multiple images of the object capturing different aspects of the object's geometry. For example, images of prostates obtained from different patients, images of an individual patient's prostate obtained at different times, images of prostates obtained from different angles, and/or images of prostates obtained with different imaging technologies may all be used to build a 3D model of a prostate. Model-based methods, as will be described in greater detail below, may be divided into appearance-based models, anatomy-informed models, mechanical models, statistical models, and combinations thereof.

One example of a type of digital image suitable for creating an object model is a magnetic resonance image (MRI). An MRI is generated by using electromagnetic fields to align the nuclear magnetization of atoms in the body in order to create an image representation of an object. After the initial alignment, radio frequency fields may be used to systematically alter the alignment, causing nuclei in the object to produce a rotating magnetic field that is detectable by a scanner. Additional magnetic fields may also be used to further manipulate the alignment in order to generate sufficient information to reconstruct an image of the object. For example, when a person lies in an MRI scanner, hydrogen nuclei (i.e., protons) may align with the strong main magnetic field. A second electromagnetic field oscillating at radio frequencies perpendicular to the main field may then be pulsed in order to push some of the protons out of alignment with the main field. When these protons drift back into alignment with the main field, they emit a detectable radio frequency signal. Since protons in different tissues of the body (e.g., fat vs. muscle) realign at different speeds, different structures of the body can be revealed in the MRI.

Similar to MRI, magnetic resonance spectroscopy imaging (MRSI) may be used as the image data from which levels of suspicion for cancer may be derived. MRSI combines both spectroscopic and imaging methods to produce spatially localized spectra from within the object. For example, magnetic resonance spectroscopy may be used to measure levels of different metabolites in body tissues. Because an MR signal produces a spectrum of resonances that correspond to different molecular arrangements of an isotope being "excited", a resonance spectrum signature may be determined and used to diagnose or plan treatment of various diseases.

A third exemplary type of digital image suitable for creating an object model according to the subject matter described herein includes a computed tomography (CT) image. Conventional CT imaging includes the use of digital geometry processing to generate a three-dimensional (3D) image of an object from a plurality of two-dimensional (2D) X-ray images taken around an axis of rotation. However, it is appreciated that other types of CT imaging may include, but are not limited to, dynamic volume CT, axial CT, cine CT, helical/spiral CT, digitally reconstructed radiograph (DRR) CT, electron beam CT, multi-slice CT, dual-source CT, inverse geometry CT, peripheral quantitative computed tomography (pQCT), synchrotron X-ray tomographic microscopy, and X-ray CT, without departing from the scope of the subject matter described herein.

Figures 3A, 3B:
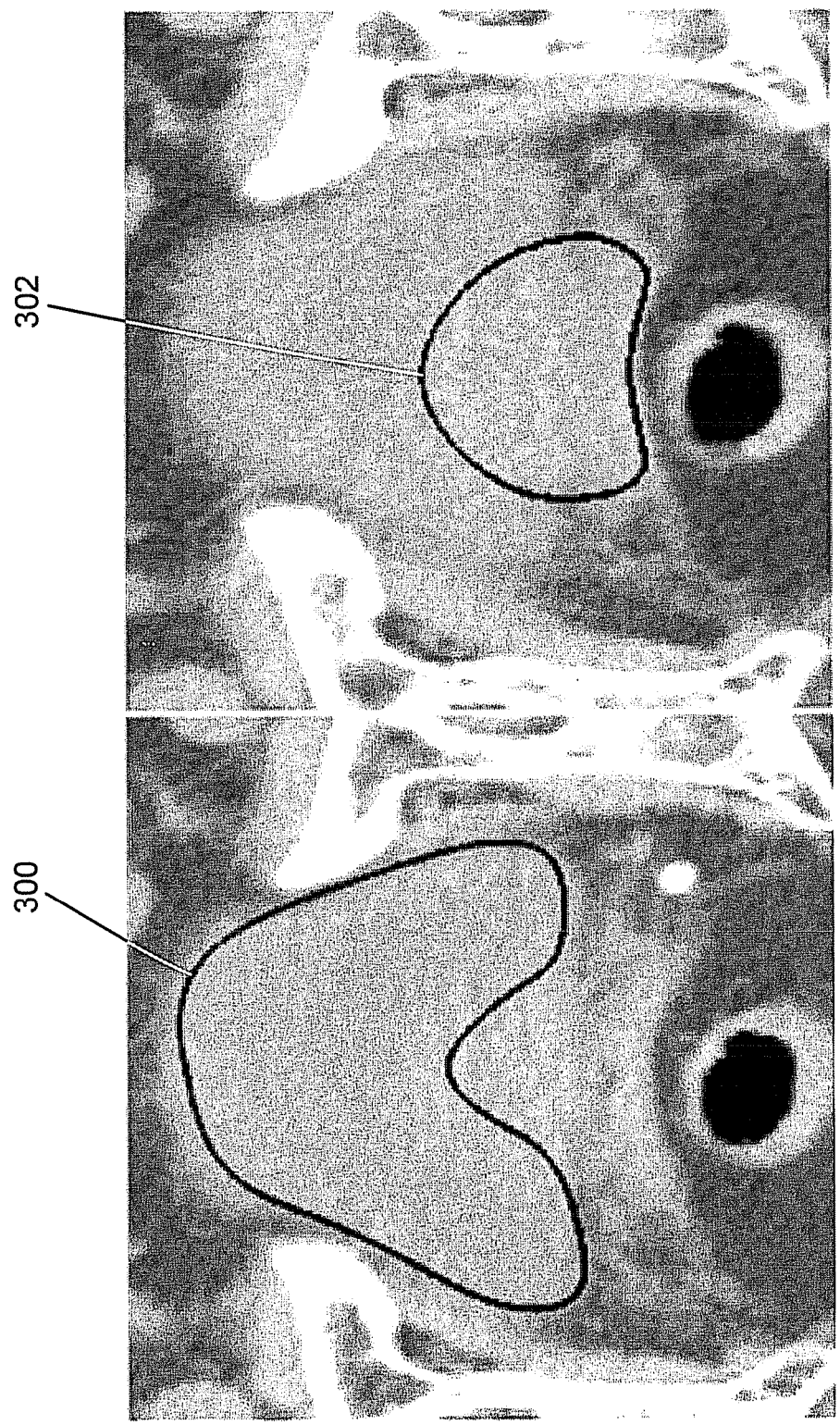
FIG. 3 is a pair of segmented CT images illustrating expert-generated boundaries of a bladder and a prostate, respectively, according to an embodiment of the subject matter described herein.

FIGS. 3A and 3B are a pair of segmented CT images illustrating expert-generated boundaries of a bladder and a prostate, respectively, according to an embodiment of the subject matter described herein. Referring to FIG. 3A, boundary 300 may correspond to the boundary of a bladder in a human male as determined by a physician through, for example, a visual inspection of pixel intensities in the image. Similarly, in FIG. 3B, boundary 302 may correspond to the boundary of a prostate in a human male based on pixel intensity patterns in the image. The manual 2D segmentations illustrated in FIGS. 3A and 3B may provide a 3D region to which a model may be fit and then used in learning probability distributions on the shape of the anatomic shape and on image information relative to the object, or it may represent a target or goal which, while achievable through slow and laborious manual methods, may be similarly (or even more accurately) performed using automated image processing and statistical object modeling methods described herein. Therefore, one measure of the accuracy of the methods described herein for segmenting planning- and intervention-guiding digital images of anatomical structures includes an image fit analysis or comparison to expert-generated manual segmentations, such as those shown in FIGS. 3A and 3B.

Create Object Model

In addition to determining a 2D boundary of an object in a 2D image, multiple 2D images of the object may be used to create a 3D model of the object. Therefore, using one or more of the high resolution digital images listed above, an initial object model may be created. As will be described in greater detail below, object models may be created according to a variety of methods. However, the goal of any of these methods is to create the most accurate description of the shape (surface and volume) and possible shape changes of the object.

Good Static Models

A static model of an object is a mathematical representation of an object, wherein the relationship of every portion of the model does not change with respect to other portions (i.e., does not deform).

However, because anatomical objects (like prostates) are rarely the same shape or size for a long period of time (i.e., not static), models of anatomical objects must also not be static if they wish to provide an accurate model of such objects.

Better Deformable Shape Models

Deformable-shape models (DSMs) are representations of both the shape and the shape variability of objects, including anatomical structures. Within the category of DSMs, however, a specialized class of DSMs, called m-reps, may best represent the specific geometries associated with anatomical objects, such as prostates.

As stated above, an "m-rep" refers to a medial-axis representation object model that is an explicit mathematical representation (i.e., a model) of an object's geometry using a set of connected continuous medial manifolds, wherein each continuous segment of the medial manifold represents a medial figure. The medial manifold may be sampled over a spatially regular lattice, wherein elements of this lattice are called medial atoms. This lattice may be in the form of a 2D mesh, or it may be a 1D chain of atoms each consisting of a cycle of spokes. As a result, m-reps may provide an efficient parameterization of the geometric variability of anatomical objects and therefore may provide shape constraints during image segmentation.

Figure 4:
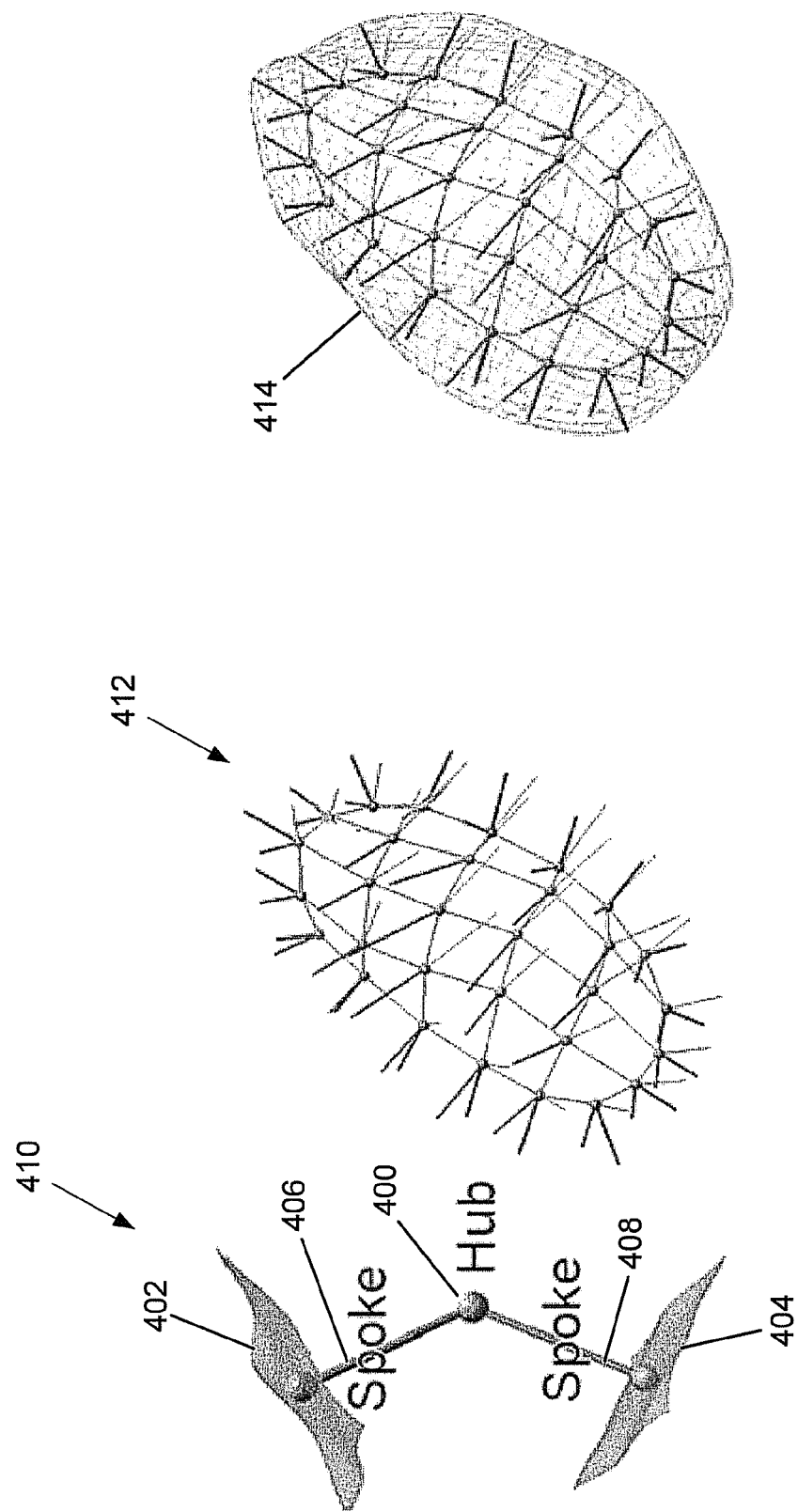
FIG. 4 is a three-dimensional representation of an m-rep object model according to an embodiment of the subject matter described herein.

FIG. 4 is a three dimensional representation of an m-rep object model according to an embodiment of the subject matter described herein. Referring to FIG. 4, medial geometry may describe objects in terms of centers and widths. A 3D object (e.g., a prostate) may be represented by a 2D curved sheet lying midway between opposing surfaces of the object, and spokes extending to the object boundary from both sides of the sheet. A position on the medial sheet, called a hub, and its two spokes are called a medial atom. Thus, using m-reps, the full object surface can be recreated from the atom spoke ends.

In FIG. 4, hub 400 may be connected to 2D curved surfaces 402 and 404 via spokes 406 and 408, respectively, and together represent m-rep 410. Multiple m-reps 410 may be combined in order to model the volumetric geometry of an object, such as object 412. Finally, a wire mesh 414 may be applied to m-rep model 412 for indicating a surface of the object. A more detailed discussion of m-reps and the process of creating m-reps is included in U.S. Pat. No. 7,200,251 which is incorporated by reference herein in its entirety.

As mentioned above, after an initial m-rep has been created using one or more high resolution digital images of an object, the m-rep may be statistically trained in order to more accurately represent the geometry of the object and/or the ways in which the object may be deformed under various conditions. The process of training an m-rep through a series of deformations and statistical computations will be described in greater detail below.

DSMs Appearance-Based

Appearance models describe images in locations that are taken relative to a geometric model. Appearance models used in segmentation are based on image intensity values. For example, voxel list and regional intensity quantile function (RIQF) methods are image intensity-based image segmentation methods. An RIQF component represents the inverse of the cumulative histogram of intensities in a particular region of an object. An RIQF may be formed by one or such components. Each component may, for example, be a 1D array of quantile function values, where each value is the intensity value for a given quantile. Each component may correspond to a different intensity, for example, the single intensity in an image, such as CT or ultrasound, or multiple intensities measured in a multi-intensity image, such as certain MR images. In addition, one or more intensities derived from the measured image, such as intensities derived by applying texture filters, may be the basis for RIQF components. There will be an RIQF for some number of different, possibly overlapping object-model-relative regions. In the embodiment shown in FIG. 5 there exists an interior region 502 and an exterior region 504. In another embodiment shown in FIG. 6 there exists 606 an interior region and an exterior centered on each spoke of an m-rep model.

DSMs

Statistically Trainable

Statistically-trainable deformable shape model (SDSM) approaches represent the underlying geometry of anatomical objects and use a statistical analysis to describe the variability of that geometry. It is appreciated that while several different geometric representations may be used to model anatomical objects, the simplest such geometry includes representing the underlying geometry in a Euclidean vector space.

Once an object is modeled, statistical shape analysis may be used to mathematically express the modes of variation of that object (i.e., describe variability of a population of geometric objects). Principal component analysis (PCA) is one example of a statistical shape analysis tool for providing an efficient parameterization of a Euclidean vector space-based object model's variability.

PCA is a vector space transform used to reduce multidimensional data sets to lower dimensions for analysis. However, PCA may only be useful for describing geometric models existing in Euclidean space (e.g., parameterized by a set of Euclidean landmarks or boundary points). As a result, PCA may not be well-suited to describing non-Euclidean representations of shape, like m-reps. Because the medial parameters used in m-reps are not elements of a Euclidean space, standard shape analysis techniques (e.g., PCA) do not apply. Therefore, a modified (i.e., generalized) form of PCA must be used for describing the variability among these types of objects.

One such modified form of PCA is called principal geodesic analysis (PGA). PGA is a generalization of PCA for curved manifolds and, like PCA, PGA may involve the calculation of the eigenvalue decomposition of a data covariance matrix in order to reduce multidimensional data sets to lower dimensions for analysis. For example, the geometry of an object may be represented by $\underline{m}$, the shape variability of the object may be represented by a probability density $p(\underline{m})$, and the image knowledge may be captured by $p(l \text{ relative to } \underline{m})$. Estimation of $p(\underline{m})$ may be accomplished by PGA, which computes object and object inter-relationship means in a way recognizing the special non-Euclidean mathematical properties of measures of orientation and size, and which computes modes of variation on an abstract flat (Euclidean) space tangent at the mean to the abstract curved space of m-reps.

As mentioned above, while m-reps may describe the geometric variability of an object in terms of bending, twisting, and widening, medial parameters are not elements of a Euclidean vector space. As a result, conventional methods for deforming m-rep models may also need to be modified to apply to a non-Euclidean vector space.

Statistically-Trained Appearance Models

Appearance models derived from DSMs $\underline{m}$ fit to training images l may be analyzed by principal component analysis to learn probability distributions on appearance $p(l \text{ relative to } \underline{m})$ to be used in computer-based segmentation. Such probability distributions can be learned both relative to planning images and relative to intervention-guiding images.

Best

Statistically-Trained (Pre-Biopsy) Patient-Specific M-Reps and Appearance Models Given a set of training images, a primary goal of training an m-rep object model is to accurately model the geometric variability of the object. Therefore, m-reps may be trained against models built by expert humans to generate statistical probability distributions that define the range of object shapes (e.g., prostates, bladders, and rectums) and the range of each object's intensity patterns in medical images across the human population of interest. As a result, the quality of the fit of an m-rep model to an image may be increased by training the m-rep.

An initial m-rep model may be automatically deformed to match target image data by altering one or more of its medial atoms so as to optimize a function formed by the sum of log $p(\underline{m})$, log $p(l \text{ relative to } \underline{m})$, and other terms providing faithfulness to initializations of the DSM. Exemplary alterations that may be performed on the medial atoms include resizing medial atoms to increase or decrease the girth of the initial model, rotating each of the spokes of the medial atoms together or separately to twist the surface of the initial model, and moving the medial atoms to bend or elongate the initial model. Because initial models may be deformed corresponding to natural operations, such as elongating, bending, rotating, twisting, and increasing or decreasing girth of the model, the amount of time and processing required to deform the m-rep to fit target image data is reduced.

In one scenario, m-rep training may include fitting m-rep models to a training population of known objects and computing a PGA, wherein PGA may be used to restrict the shape of the model to statistically feasible instances of the object.

Training procedures for an object's geometry, given by $p(\underline{m})$, and the geometry-to-image match, given by $p(l \text{ relative to } \underline{m})$, use training cases in which an expert user has produced a careful manual segmentation of the object(s), from which binary images can be produced. In each training case, an m-rep is closely fitted to the binary image for each object, and PGA of the aligned fits yields $p(\underline{m})$. To find $p(l \text{ relative to } \underline{m})$ the resulting fits are used to extract the prostate-related RIQFs for all model-relative regions from the corresponding training image. The method for fitting $\underline{m}$ to the binary images is a variant of the greyscale segmentation method described above: the objective function, log $p(l \text{ relative to } \underline{m})$+log $p(\underline{m})$, is replaced by a function of the same form, image match+ geometric typicality, but where binary image match is computed from distances between the binary and the boundary implied by $\underline{m}$, and where geometric typicality rewards smoothness, non-folding, and geometric regularity of $\underline{m}$.

After an m-rep is initialized, that is, roughly positioned and oriented to correspond to the object, the m-rep may be deformed by optimizing an objective function that includes, for example, image intensity and/or non-intensity terms that compute a measure of the quality of the match between the deformed DSM and the target image.

Segmentation

Step 1

Initialization

Shape is often defined as the geometry of an object that is invariant under global translation, rotation, and scaling. Therefore, in order to ensure that the variability being computed is from shape changes only, one must align the training objects to a common position, orientation, and scale. One common alignment technique includes minimizing, with respect to global translation, rotation and scaling, the sum-of squared distances between corresponding data points.

Thus, an exemplary m-rep initialization algorithm may include steps consisting of (1) translation, (2) rotation and scaling and (3) iteration. For example, translation may include centering a plurality of m-rep models to an image by translating each model so that the average of its medial atoms' positions is located at an arbitrary origin point. A particular model may then be selected and aligned to the mean of the remaining models. This process may be repeated until the alignment metrics cannot be further minimized.

Another exemplary m-rep initialization algorithm may include not only translation, rotation, and scaling, but also, after that, deformation within statistically feasible instances of the object, as described in the next section, with iteration between the translation, rotation, and scaling, on the one hand, and deformations, on the other hand.

Segmentation

Step 2

Deformation

Methods based on analysis of shape variation are becoming widespread in medical imaging. These methods allow a statistical modeling of prior shape knowledge in tasks where the image information itself often is not strong enough to solve the task automatically. One example of the use of deformable models in segmentation includes determining the preferred deformations by a statistical shape model. Another important task is shape analysis and classification, where a statistical shape model provides distributions of healthy and diseased organs for diagnostic methods.

The most common type of statistical shape model consists of a mean shape with deformations. The mean and the corresponding deformations are constructed through statistical analysis of shapes from a collection of training data. Each shape in the training set is represented by the chosen shape representation, and analysis of the parameters for the representation gives the mean and variations.

Another type of statistical shape model consists of an initialization from previous deformation of a mean and deformations from that initialization. An example is the deformations from an m-rep segmented from a planning image into an m-rep segmented from an intervention-guiding image.

It is appreciated that m-reps can be trained on shapes derived from different images of the same patient and/or across images of different patients. Same-patient training provides statistics that describe shape differences due to mechanical forces acting on the prostate, e.g., different degrees of rectal and/or bladder filling, and by natural differences that occur between patients. Training from images from different patients provides statistics that describe anatomic differences between individual patients.

Deformation

Appearance-Based

Pixel Intensity

As mentioned above, PGA may be applied to m-reps, wherein the m-reps may express the geometry of the object in terms of p(m). PCA may be applied to RIQFs for regions relative to $\bar{m}$, wherein the RIQFs express the object-relative appearance in terms of p(l relative to m). Therefore, in order to make l relative to m be amenable for PCA, pixel intensities for both exterior and interior regions adjacent to the object boundary may be represented by the RIQF describing a region near and interior to the object boundary implied by $\bar{m}$, wherein the RIQF represents the inverse of the cumulative histogram of intensities in the region.

Figure 5:
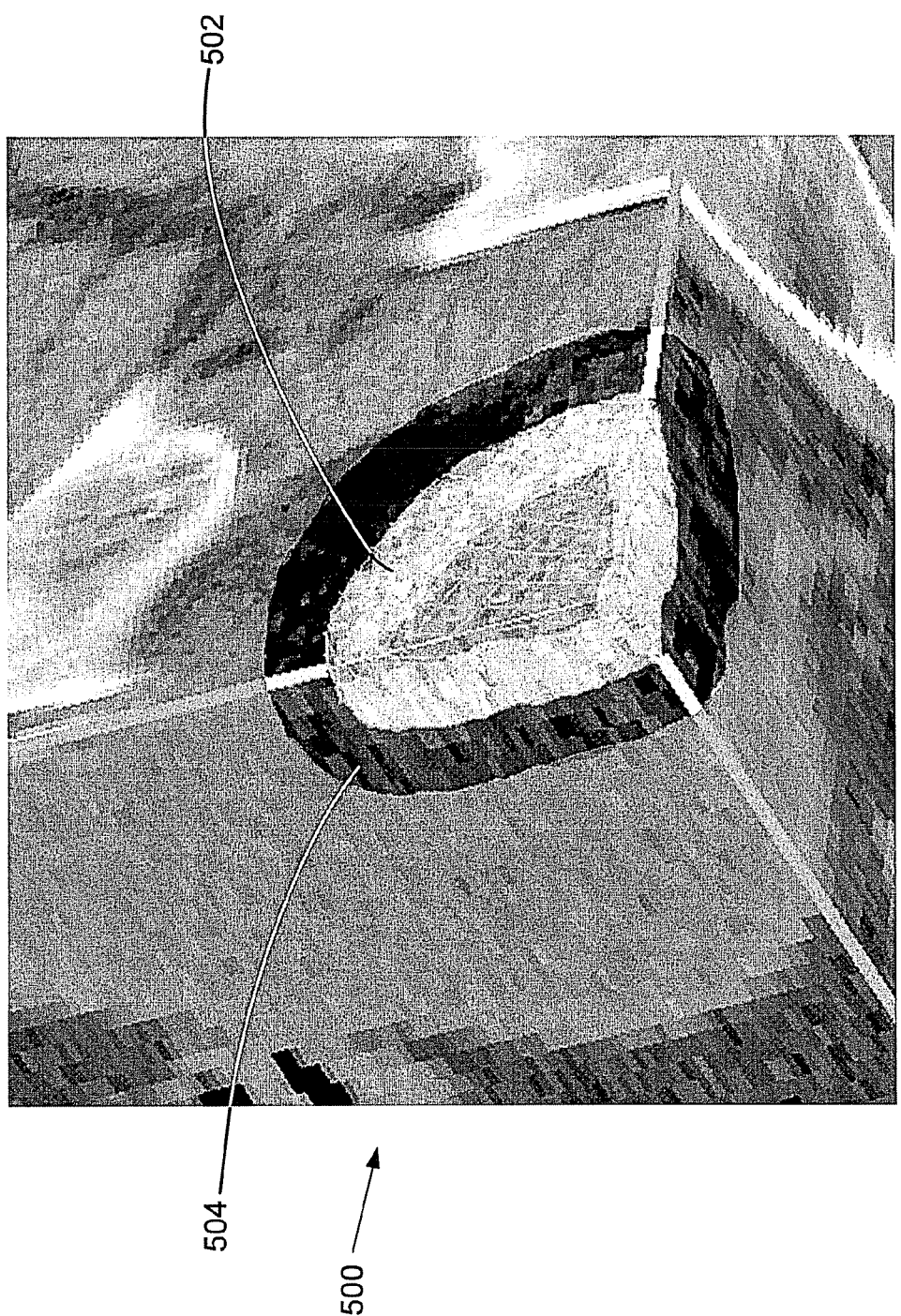
FIG. 5 is a triorthogonal representation of a prostate in a CT image suitable for sampling image intensity values according to an embodiment of the subject matter described herein.

FIG. 5 is a triorthogonal representation of a prostate in a CT image suitable for sampling image intensity values according to an embodiment of the subject matter described herein. Referring to FIG. 5, triorthogonal CT display 500 includes region 502 for sampling image intensities inside of a prostate and region 504 for sampling image intensities outside of the prostate. Sampling image intensities in both the interior and exterior regions adjacent to the object boundary using a function describing a region near and interior to the object boundary by the RIQF for the object may be necessary for allowing the object's geometry to be appropriate for PCA.

Figure 6:
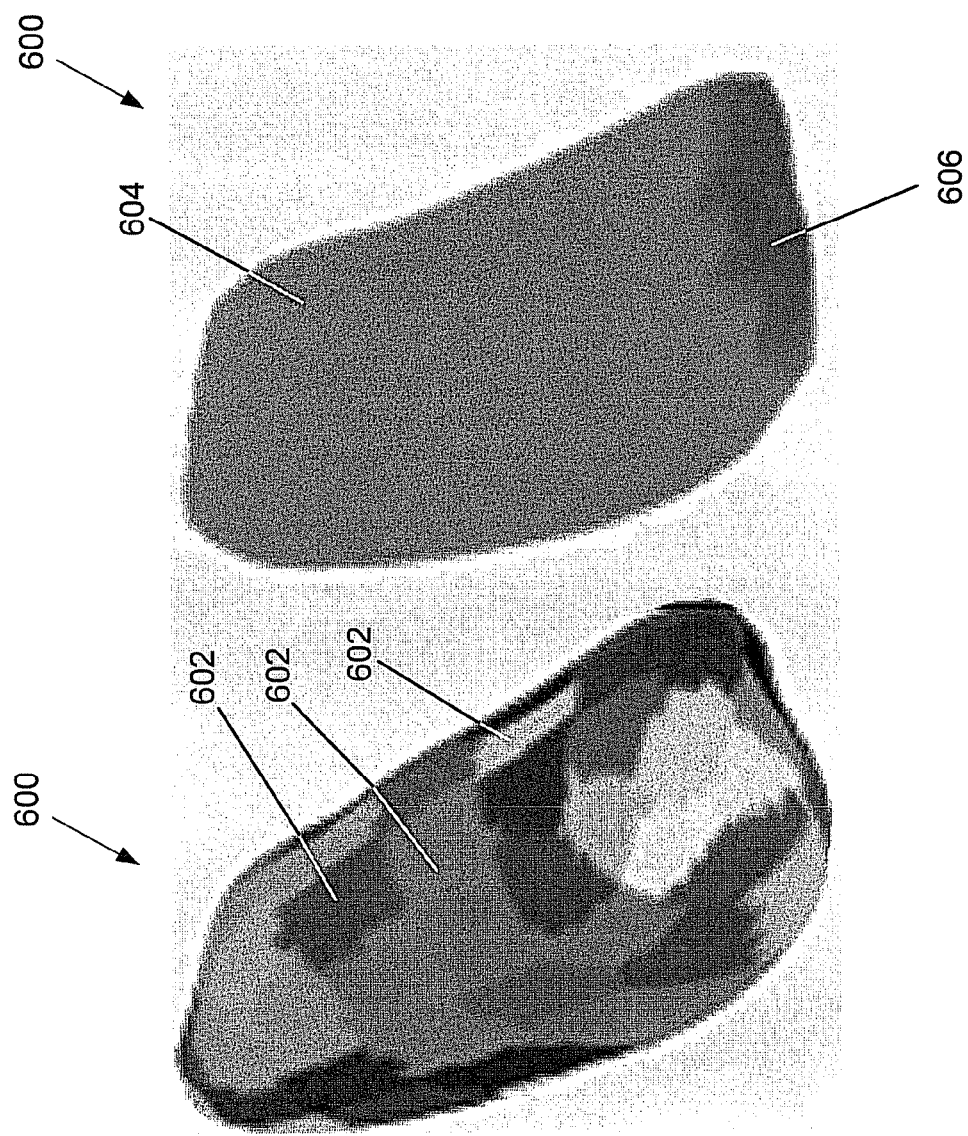
FIG. 6 includes representations of exemplary m-rep object models before and after RIQF analysis is performed according to an embodiment of the subject matter described herein.

FIG. 6 includes representations of an exemplary m-rep object model prepared for RIQF analysis according to an embodiment of the subject matter described herein. On the right, the bladder m-rep object model 600 is shown. On the left, object 600 may be defined by a boundary and spoke-related regions 602 defined based on the m-rep. Spoke-related regions 602 may then be used to form interior and exterior regions corresponding to each spoke, and these regions may be used to provide an RIQF-based appearance model for each region. The idea is that regions of homogeneous tissue are in the same positions relative to the target object in different patients will have comparable tissue compositions. An improved appearance model will be obtained by allowing exterior regions on the object boundary defined by these clusters in training to slide around when they are used to define exterior regions whose RIQFs contribute to the image match.

Figure 7:
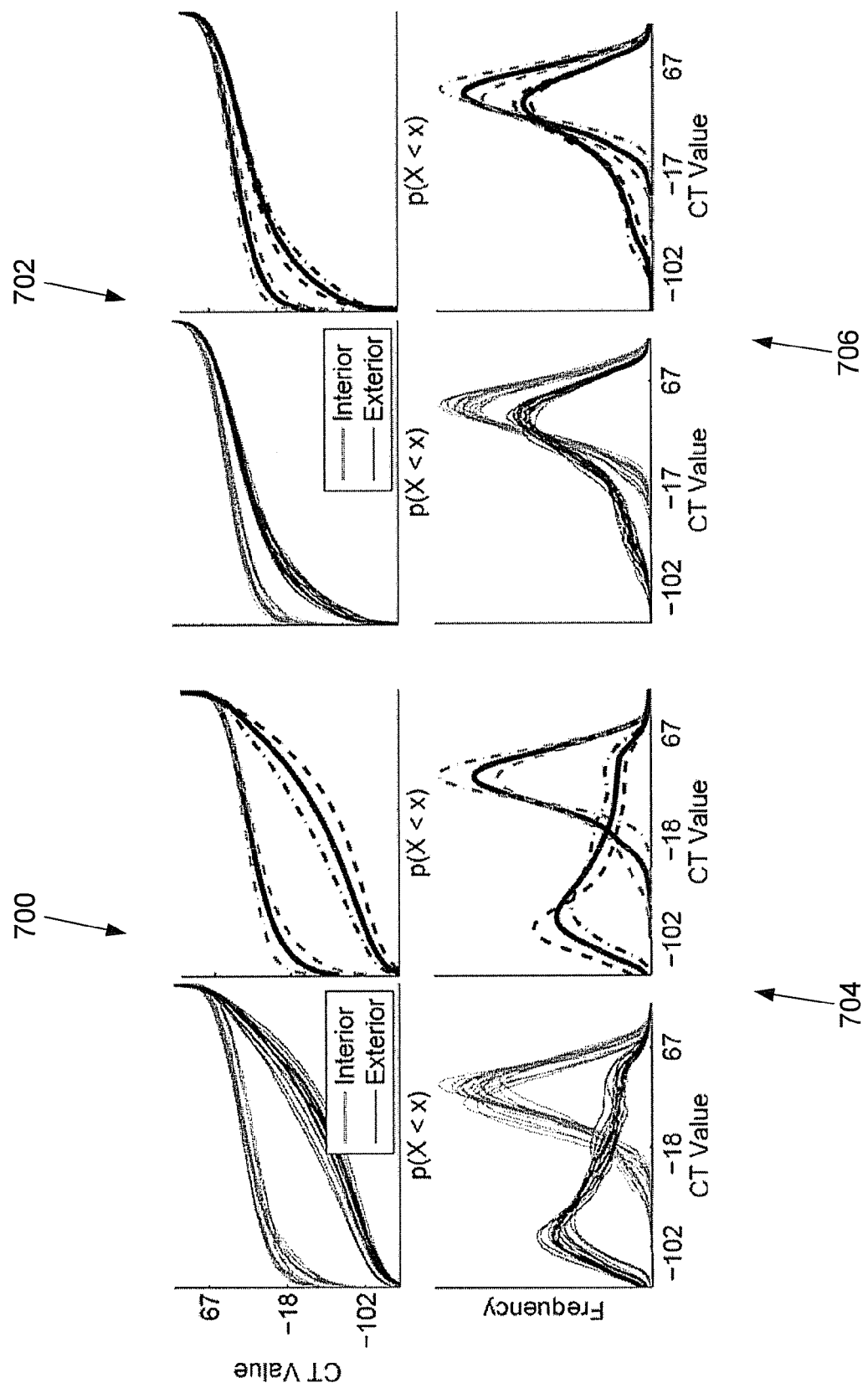
FIG. 7 is a series of plots of various statistical measures of RIQF image fit for a bladder according to an embodiment of the subject matter described herein.

FIG. 7 is a series of plots of RIQFs (top) and histograms derived therefrom (bottom) for a bladder and for a prostate, derived from training images, according to an embodiment of the subject matter described herein. Referring to FIG. 7, image pair 700 illustrates RIQFs for a bladder object and image pair 702 illustrates RIQFs for a prostate object, wherein the first and third columns show the RIQFs and histograms from the training images, and the dashed curves in the second and fourth columns represent ±1.5σ from the mean (represented by solid lines). Image pairs 704 and 706 represent histograms corresponding to RIQFs 700 and 702, respectively.

Deformation

Appearance-Based

Texture Features

In one example, for certain images, texture features provide important separators of an object from its background that are not possible using intensity variables alone. According to one aspect, as used herein, the terms "texture" and "texture feature" include a collection of one or more pixels in a digital image having related elements. According to another aspect, a texture can include a spatial arrangement of texture primitives arranged in a periodic manner, wherein a texture primitive is a group of pixels representing the simplest or basic subpattern. A texture may be, for example, fine, coarse, smooth, or grained, depending upon the pixel intensities and/or the spatial relationship between texture primitives.

For example, in CT, the pattern of bronchi and blood vessels within the lobes of the lung can be important for segmentation of the lobes or of the lung from the heart. Segmentation by posterior optimization of m-reps suggest that improved segmentations are obtained in some cases when RIQFs on the texture variables are concatenated with RIQFs on intensity variables.

According to one embodiment, six 2D rotationally invariant texture features in the plane perpendicular to the ultrasound probe may be used. Next, filters may be applied to the texture features, including but not limited to, a Gaussian and a Laplacian filter. Additionally, the maximum response may be taken over multiple orientations of either a first derivative or a second derivative Gaussian. Each texture feature may also be evaluated by its ability to discriminate the interior and exterior of the prostate based on the Mahalanobis distance of the mean interior description to the mean exterior description, and vice versa.

For example, using the experimental data described herein, the texture feature that performed the best at the global scale was based on a small-scale second-derivative Gaussian filter. It is appreciated that for global interior and exterior regions, this feature is 2.9 times more sensitive than using intensity alone. Thus, intensity RIQFs together with texture RIQFs may provide a basis for a strongly discriminating image match term for the objective function described in.

In this case, the texture feature was the maximum over orientations in the image planes of the result of convolution with the oriented $2^{nd}$ derivatives of a Gaussian. This measure was chosen because it showed good separation between the RIQFs for a global region external to the prostate and a global internal region.

Deformation

Anatomy-Informed

In addition to using image intensity patterns alone, successful segmentation of an image may depend on both knowledge of the anatomy and the image intensity patterns relative to the anatomy. Therefore, segmentation may be limited to anatomically reasonable instances of the target object geometry. Knowledge of the anatomy may be captured by a probability density $p(\underline{m})$ on the representation $\underline{m}$ of the geometry of the object(s) in question, and the image knowledge is captured by $p(l\ \text{relative to}\ \underline{m})$, which we take to be equal to the conditional probability $p(l|\underline{m})$.

Segmentation may then consist of:

i) limiting $\underline{m}$ to a space S covering only the primary modes corresponding to geometrically non-folding, smooth structures that reasonably represent the organ in question; and ii) finding the most probable such $\underline{m}$ given the image intensity patterns represented by l.

That is, to segment the anatomic object(s) represented by $\underline{m}$, $\arg\max_{m \in S} p(\underline{m}|l) = \arg\max_{m \in S} [\log p(l|\underline{m}) + \log p(\underline{m})]$ may be computed by conjugate gradient optimization of $(\log p(l|\underline{m}) + \log p(\underline{m}))$ over the coefficients of the primary modes of variation exhibited in $p(\underline{m})$. Alternatively, the function optimized may in addition include a term reflecting deviations from information provided at the time of initialization.

In order to allow the estimation of the functions, $p(\underline{m})$ and $p(l\ \text{relative to}\ \underline{m})$, it is necessary that the representation of both $\underline{m}$ and of l relative to $\underline{m}$ be appropriate for PGA and that both functions richly describe the geometry and the image intensity patterns, respectively. Therefore, as described above, $\underline{m}$ may be represented using m-reps and $\underline{m}$ may be described using RIQFs according to the subject matter described herein.

Experimental Results

Figure 8:
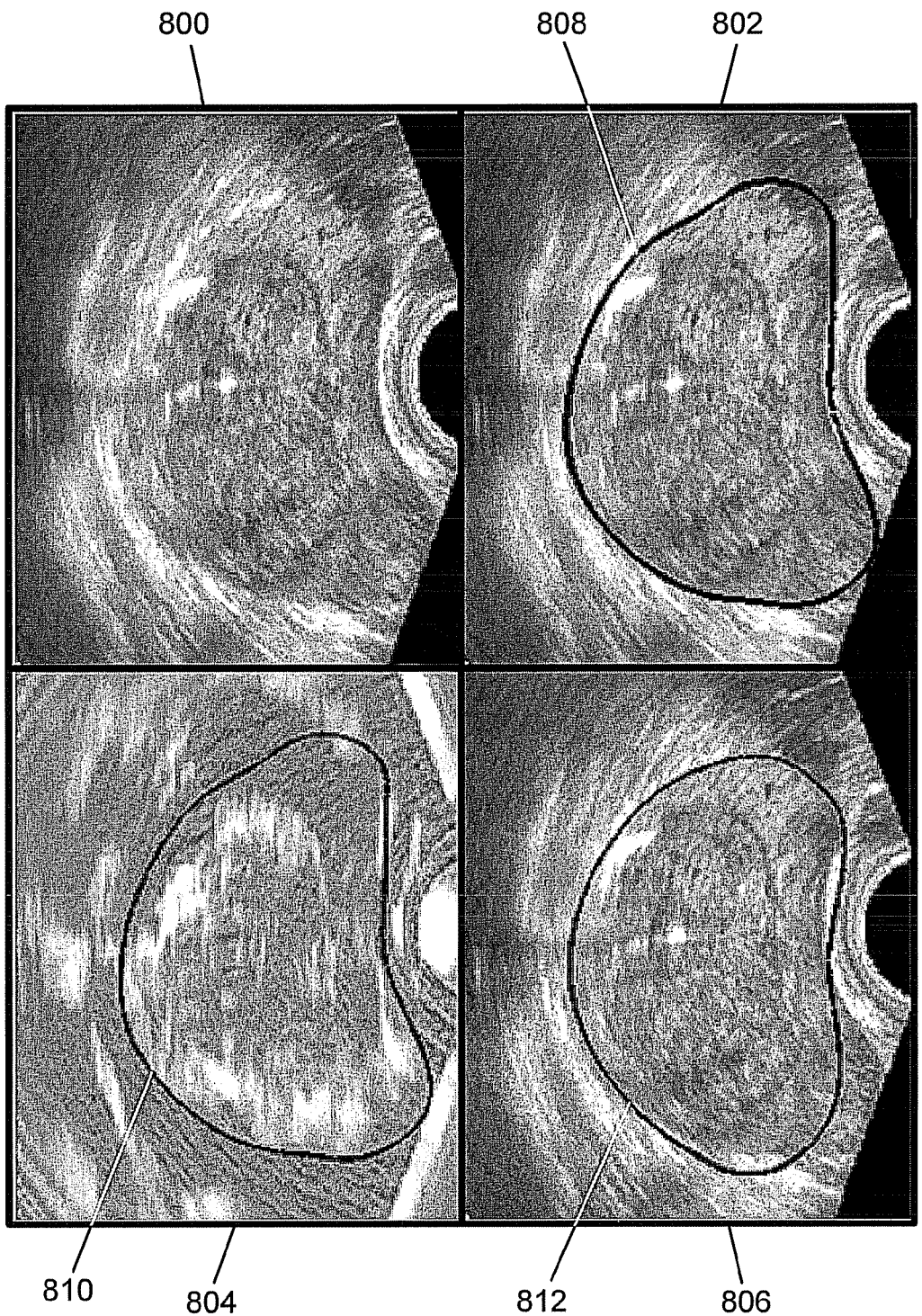
FIG. 8 is series of exemplary TRUS images illustrating prostate boundaries generated using various methods according to an embodiment of the subject matter described herein.

FIG. 8 is a series of exemplary TRUS images illustrating prostate boundaries generated using various methods according to an embodiment of the subject matter described herein. Referring to FIG. 8, TRUS image 800 is an unsegmented image of a prostate sliced through the middle of the prostate, image 802 illustrates manual segmentation boundary 808, image 804 illustrates a $2^{nd}$ derivative of Gaussian based texture parameter relative to the manual segmentation boundary 810, and image 806 illustrates a segmentation boundary 812 via posterior optimization of m-reps with an intensity-and-texture-RIQF based appearance model. It is appreciated that the inaccuracy of the segmentation boundary 812 shown in image 806 is the result of not accounting for the cutoff of the prostate in the image.

FIG. 9A is a surface representation of a bladder and a prostate. FIG. 9B is a representation of a prostate and bladder including an automated segmentation of each.

Figure 10C:
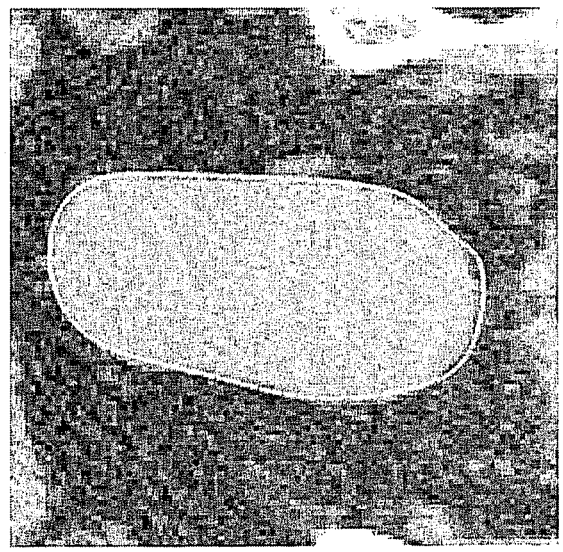
FIG. 10C is a midaxial slice of a bladder showing computer-based segmentation according to an embodiment of the subject matter described herein.
Figure 10B:
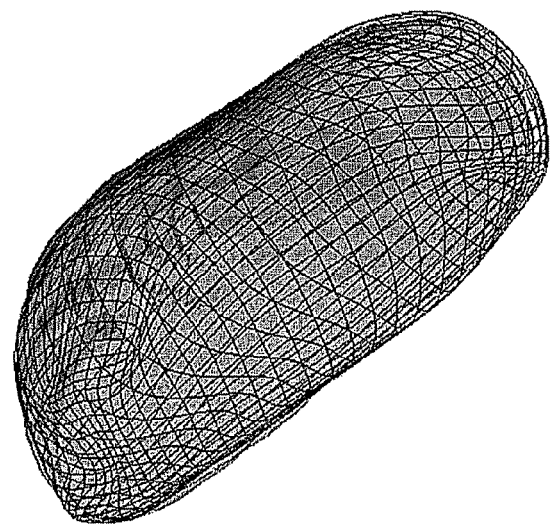
FIG. 10B is a representation of a bladder including human expert segmentation and computer-based segmentation according to an embodiment of the subject matter described herein.
Figure 10A:
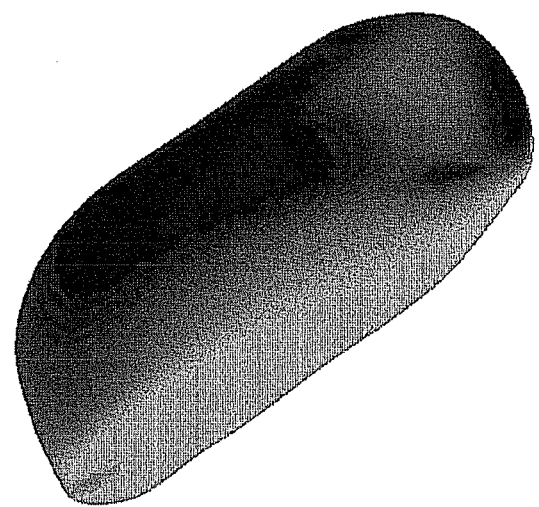
FIG. 10A is a surface representation of a bladder according to an embodiment of the subject matter described herein.

FIG. 10A is a surface representation of a bladder. FIG. 10B is a representation of a bladder including human expert segmentation and computer-based segmentation. FIG. 10C is a midaxial slice of a bladder including an automated segmentation.

Figure 11A:
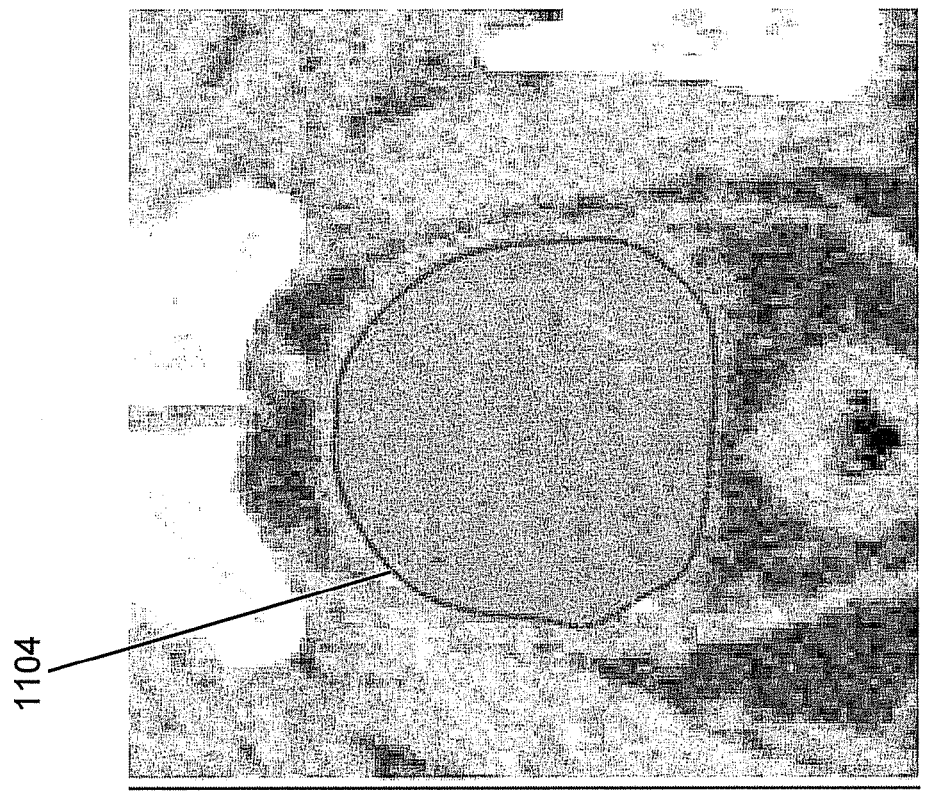
FIG. 11A is a 3-dimensional representation of a prostate including human expert segmentation and computer-based segmentation according to an embodiment of the subject matter described herein.
Figure 11B:
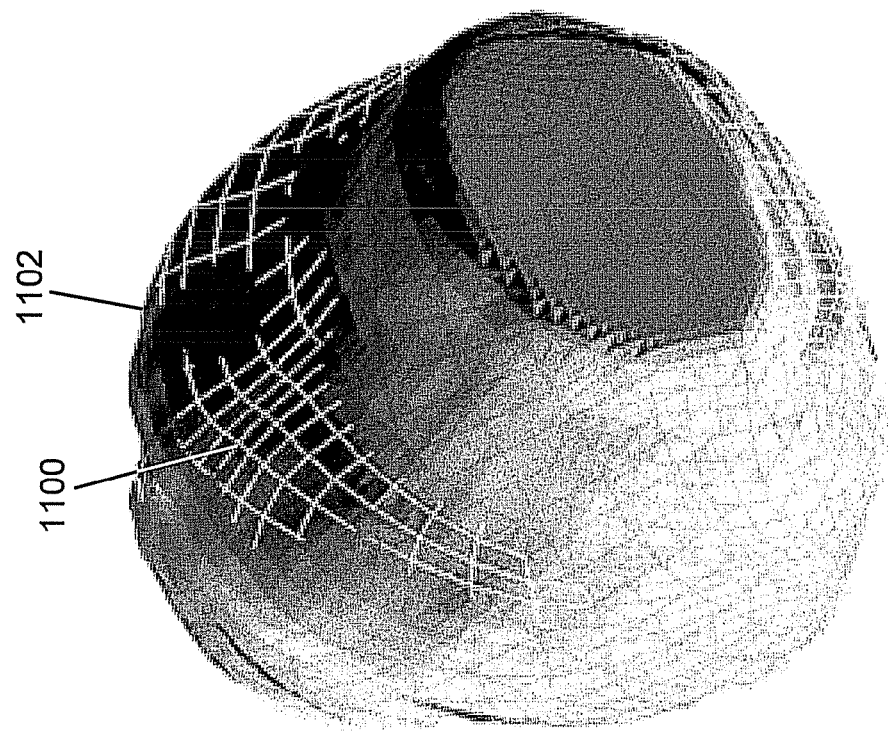
FIG. 11B is a slice of a prostate in a CT scan showing computer-based segmentation according to an embodiment of the subject matter described herein.
Figure 12:
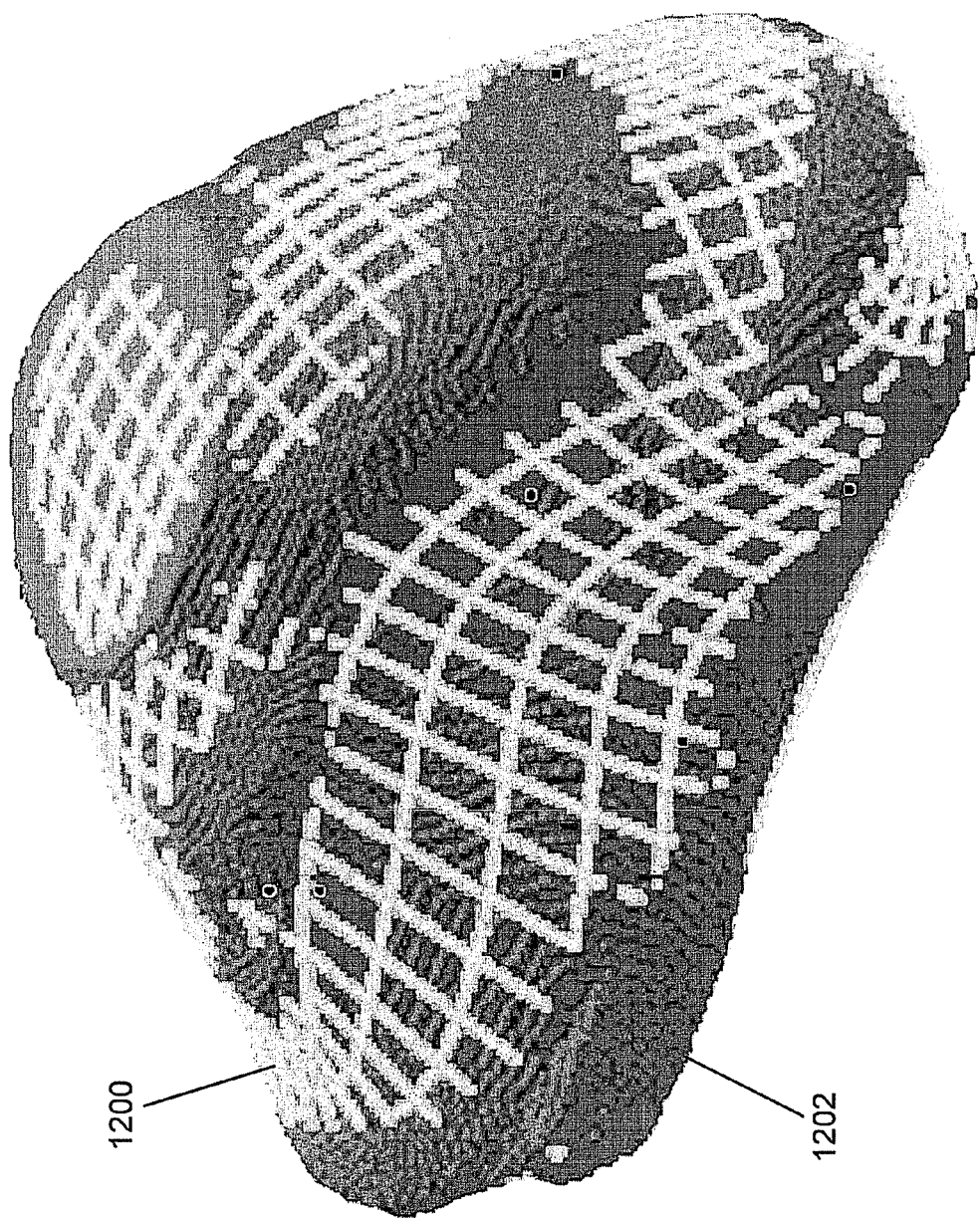
FIG. 12 is a 3-dimensional representation of a prostate including human expert segmentation and computer-based segmentation.

FIG. 11A is a 3D representation of a prostate including human expert segmentation and computer-based segmentation. Referring to FIG. 11A, wire mesh 1100 illustrates a 3D prostate boundary automatically generated by software 128 according to an embodiment of the subject matter described herein. Surface 1102 illustrates a surface boundary of the prostate manually generated by a human expert. FIG. 11B is an CT slice of a prostate, wherein prostate boundary 1104 corresponds to boundary 1100 shown in FIG. 11A. Similarly, FIG. 12 is a 3D representation of a prostate including automated segmentation boundary 1200 and human expert segmentation boundary 1202.

Figure 13:
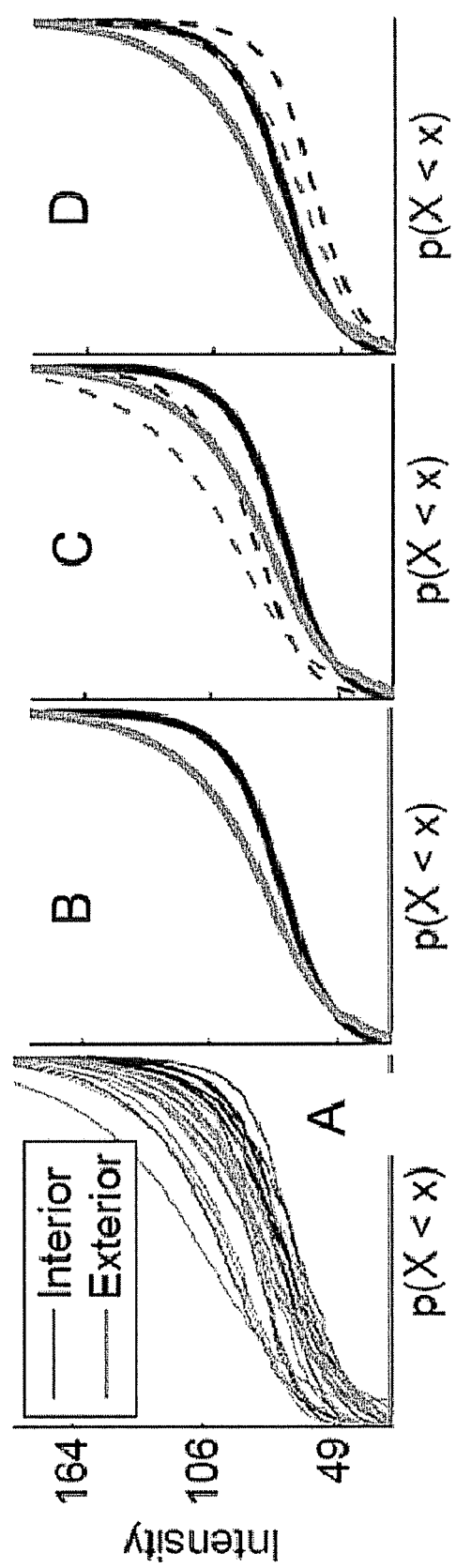
FIG. 13 is a series of plots illustrating various statistical measures of image fit according to an embodiment of the subject matter described herein.

FIG. 13 is a series of plots of RIQFs according to an embodiment of the subject matter described herein. Referring to FIG. 13, figure A illustrates texture RIQFs for interior and exterior global regions for a prostate. Figure B illustrates mean RIQFs for the prostate. Figures C and D illustrate mean RIQFs and ±1.5 a from the mean.

Figure 14:
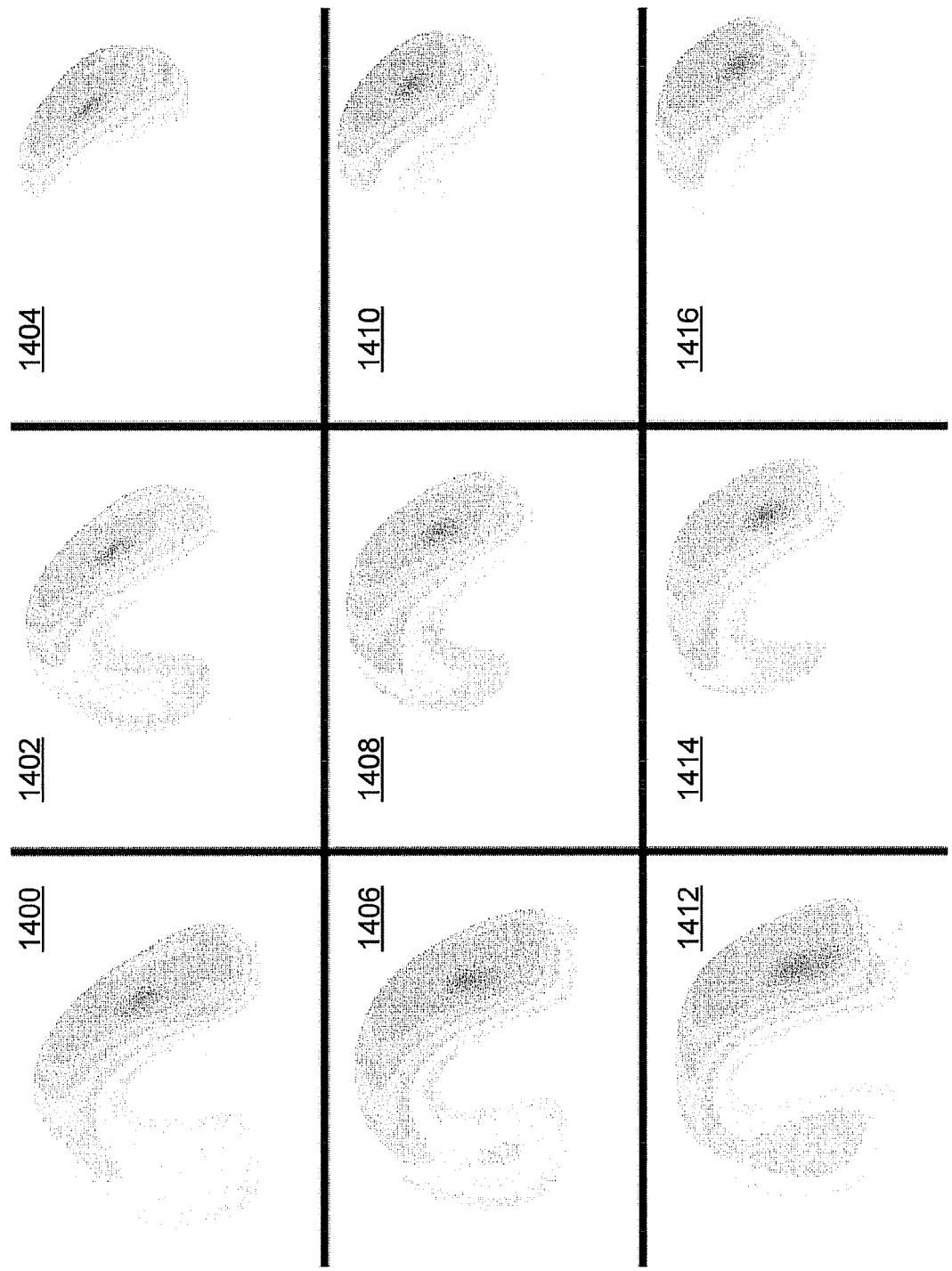
FIG. 14 is a series of samples from the first two eigenmodes computed from a plurality of m-reps fit to human-generated contours according to an embodiment of the subject matter described herein.

FIG. 14 is a series of samples from the first two eigenmodes computed from a plurality of m-reps fit to human expert generated contours according to an embodiment of the subject matter described herein. Referring to FIG. 14, results of PGA are illustrated, wherein the mean m-rep is m-rep 1408. Rows (m-reps 1400-1404, 1406-1410, and 1412-1416) range from −1.5 σ to +1.5 σ along the first mode and columns (m-reps 1400, 1406, 1412; 1402, 1408, 1414; and 1404, 1410, 1416) go from −1.5 a to +1.5 σ along the second mode. The first mode captures global scaling across patients while the second mode captures the saddle-bag appearance at the prostate/rectum interface.

Figures 15A, 15B, 15C:
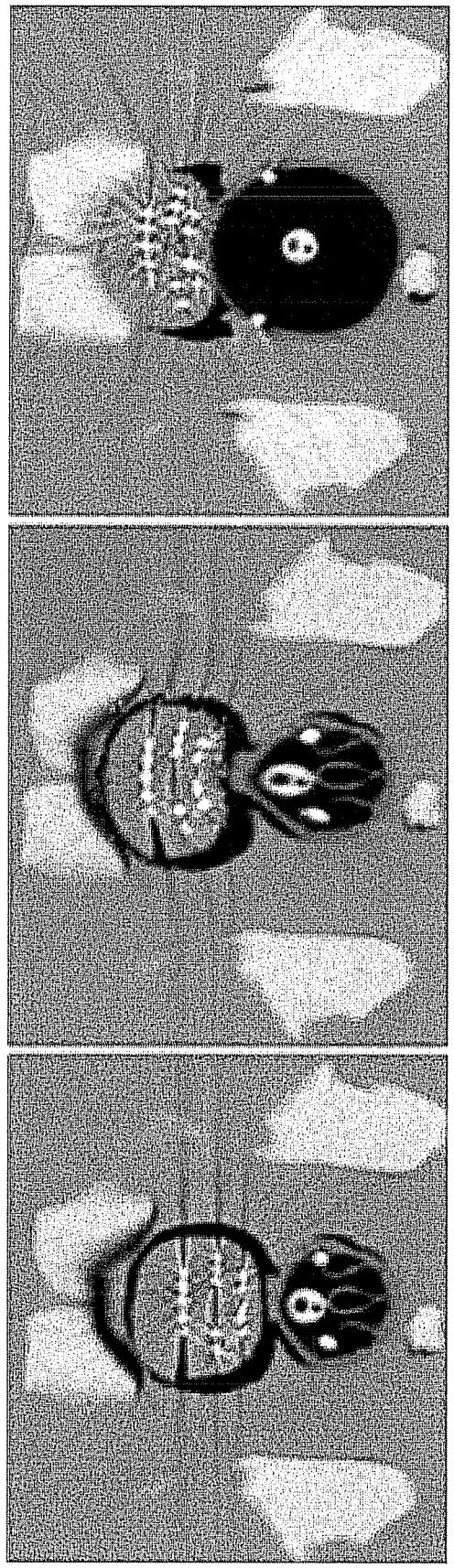
FIGS. 15A-15C are CT scans of a male pelvis phantom according to an embodiment of the subject matter described herein.

FIGS. 15A-15C is series of CT scans of a male human pelvis. Referring to FIG. 15A, the CT slice illustrates a male pelvis phantom with a deflated rectal balloon. FIG. 15B illustrates a FEM-computed slice with an inflated rectal balloon. FIG. 15C illustrates an actual CT slice with an inflated rectal balloon.

Deformation

Mechanical Simulation

As described above, m-reps provide a framework for automatically building 3D hexahedral meshes for representing the geometry of anatomical objects such as prostates. In order to simulate a multitude of possible deformations of the m-rep, physically correct mechanical deformations may be computed, one example of which includes the finite element method (FEM). As used herein, FEM is a numerical technique for finding approximate solutions to partial differential equations and integral equations by either eliminating the differential equation completely or approximating the equation using ordinary differential equations, which are then solved using standard techniques. Other techniques may also be used without departing from the scope of the subject matter described herein.

Each quadrilateral in the medial atom mesh forming an m-rep forms two quadrilaterals of spokes, one on each side of the medial sheet. Each quadrilateral of spokes forms a 6-sided entity, which can be further subdivided by spoke subdivision and interpolation. The resulting refined mesh can be embedded in a mesh fit to the exterior of an anatomic object, possibly including other objects. To simulate the effect of forces on this region or to fit a deformation by mechanically reasonable deformations, the overall mesh can be used to solve the mechanical differential equations of the well-established FEM method.

Thus, object model deformations caused by internal forces may be learned by mechanical modeling techniques such as FEM, and statistics of the resulting deformations can be derived to m-reps extracted from the FEM results.

This capability has been validated using CT scans of a tissue equivalent pelvis phantom with metallic seeds implanted in the prostate and an endorectal balloon catheter. It is appreciated that calculations were 3D, but 2D results are shown for clarity. Seeds in the un-deformed prostate were mapped to corresponding positions in the prostate deformed by the inflated balloon with an accuracy limited only by CT voxel size. This method can be applied to compute physically correct deformations on m-reps fit to training images to generate additional m-reps for geometric training, and to validate the spatial accuracy of an atlas mapped via a trained m-rep.

Carrying the Intervention Target Region to the Intervention-Guiding Image

The intervention target region that has been extracted from the planning image or another image registered with it forms a subregion of the m-rep of the anatomic object segmented from the planning image. In one example the planning image is an MRI, the anatomic object is the prostate, and the intervention target region is tissue portrayed as suspicious for cancer in an MRS image. The deformation of the m-rep between its form segmented in the planning image and its form in the intervention-guiding image yield a transformation of all points in the object interior, according to the rule that corresponding positions, according to proportion of length, on corresponding spokes map into each other. This deformation can be applied to the intervention target region in the anatomic segmented from the planning image to provide the predicted intervention target region in the intervention-guiding image.

Training and Segmentation

Overlay M-Rep onto Intervention-Guiding Image(s)

Figure 16:
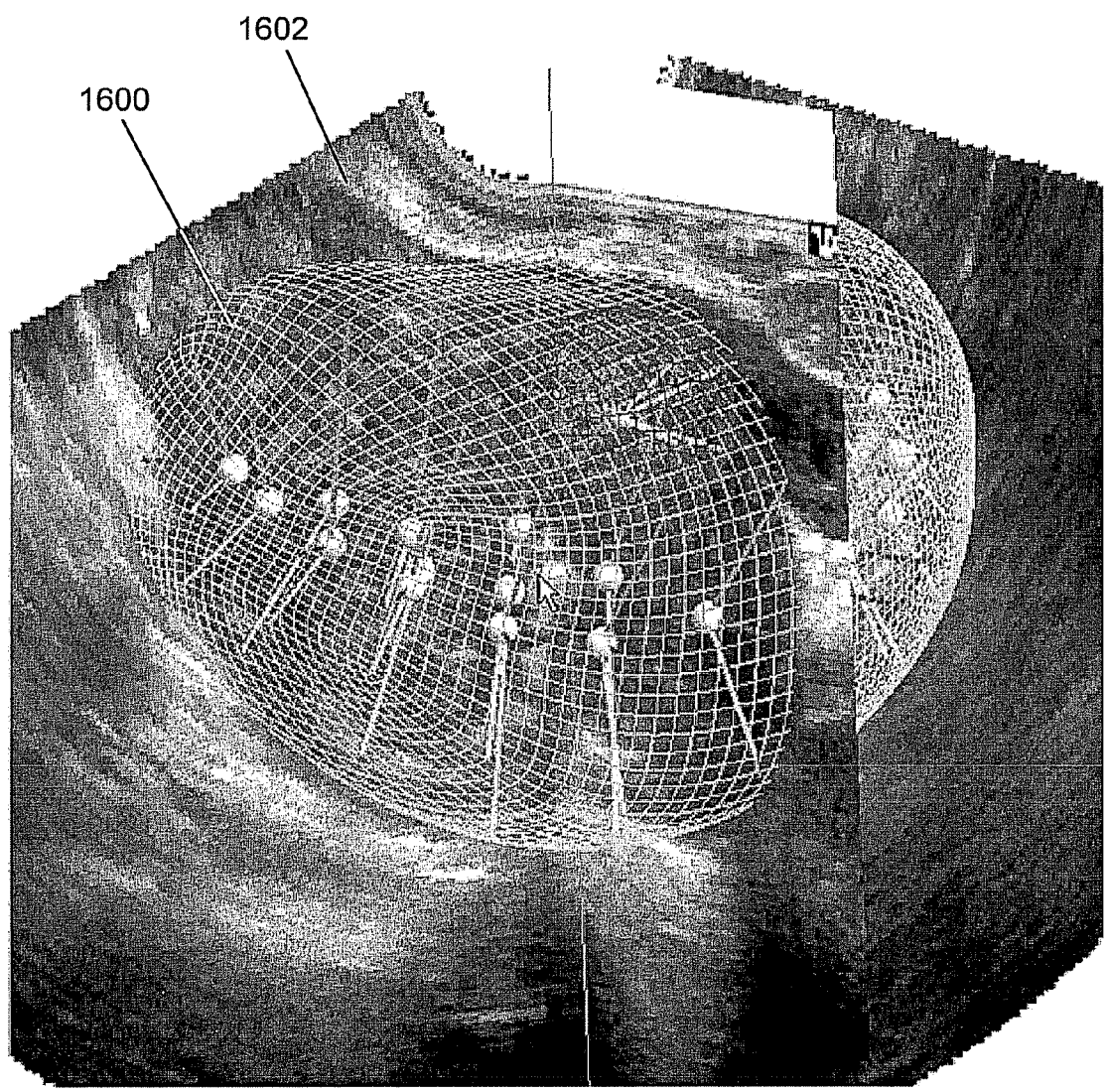
FIG. 16 is an exemplary display of a 3D m-rep model overlaid onto a TRUS image of a prostate for guiding a physician's needle during a biopsy procedure according to an embodiment of the subject matter described herein.

FIG. 16 is an exemplary TRUS image including an overlaid image of an m-rep boundary of an object of interest according to an embodiment of the subject matter described herein. Referring to FIG. 9, a 3D TRUS image of the prostate is shown where m-reps were fit to the human contours for the images yielding a median volume overlap (i.e., Dice coefficient) of 96.6% and a median average surface separation of 0.36 mm. As used herein, the Dice similarity coefficient (DSC) defines the area/volume overlap between sets A and B as $2|A \cap B|/(|A|+|B|)$. A shape model representation derived from a noisy TRUS image should aim for an equally good overlap. The fits shown in FIG. 9 are excellent and meet the requirements for providing mapping a planning image of an object comprising an anatomical structure to intervention-guiding object image data and thereby providing a mapping of the intervention target region within the anatomical structure from the planning image into the intervention-guiding image.

Potential Applications

According to one aspect, the subject matter described herein may be used to guide image-guided needle interventions. For example, given one or more images, an m-rep model may be fit to an object within the planning image (e.g., a prostate) and the m-rep model fit to the object in the intervention-guiding image and the mapping of an intervention target region between the images may be used to guide a physician's biopsy needle during biopsy or surgery.

Figure 17:
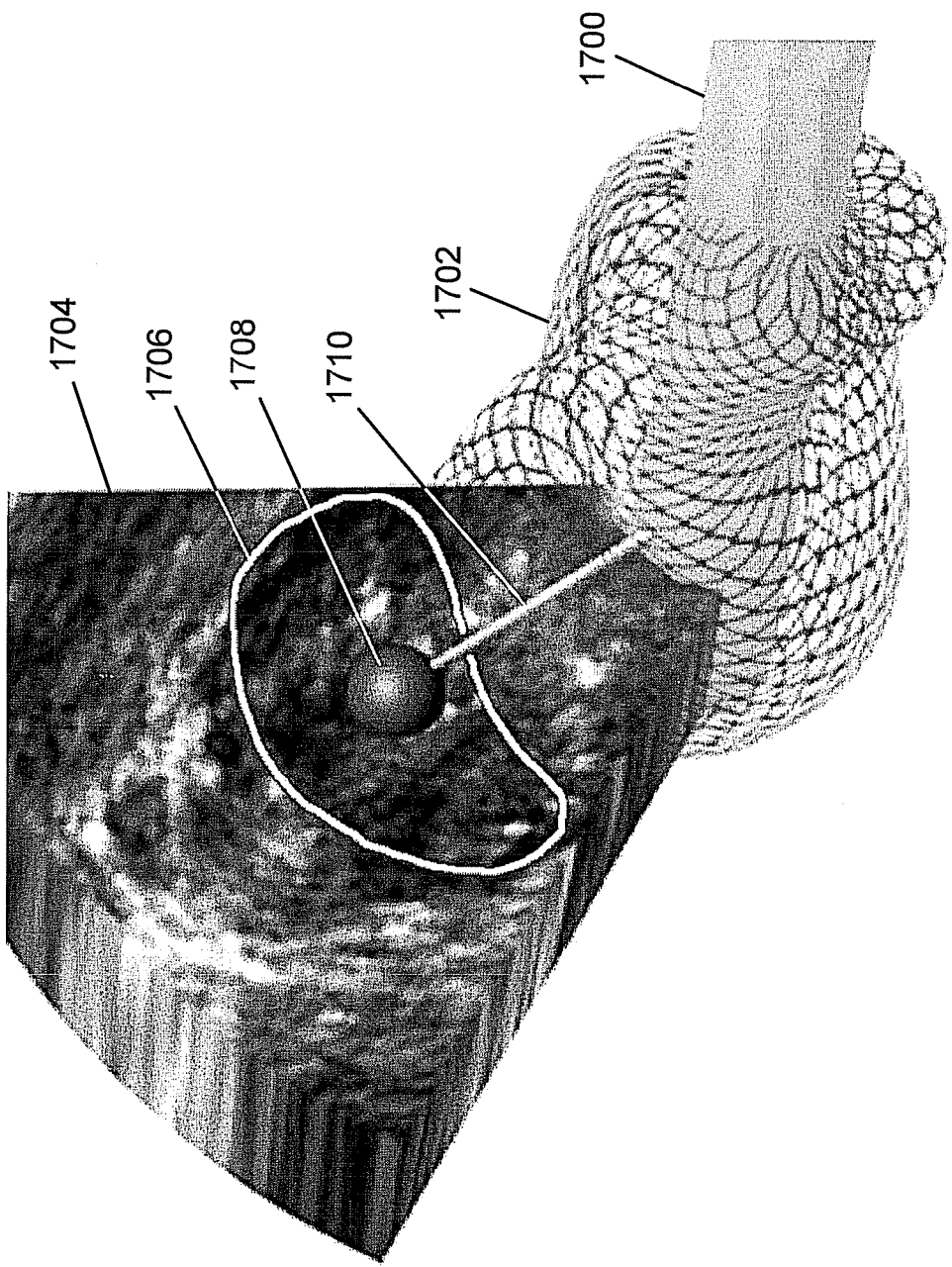
FIG. 17 is a diagram illustrating an exemplary system for providing mapping of an object comprising an anatomical structure from planning image data to intervention-guiding image data according to an embodiment of the subject matter described herein.

For example, FIG. 17 is a diagram illustrating the guiding of a biopsy needle into a prostate with the guidance of a patient-specific prostate m-rep and a target intervention region overlaid on a TRUS image according to an embodiment of the subject matter described herein. Referring to FIG. 17, transrectal ultrasound probe 1700 may be inserted into rectum 1702 of a patient. As a result, probe 1700 may generate a TRUS image 1704 of the area surrounding the patient's prostate and display the image on a display device. An m-rep model of the patient's prostate may then be overlaid on TRUS image 1704, wherein the m-rep may help define a prostate boundary 1706. Within prostate boundary 1706, the target intervention region 1708 may be portrayed. For example, a portion of the prostate that is suspicious for cancer may be biopsied using needle 1710. As described in greater detail above, biopsy needle 1710 may be guided to target object 1708 more accurately, and thus without disturbing other tissue, through the use of m-reps to accurately display object boundary 1706 on an intervention-guiding image, such as TRUS image 1704.

In another example, needles used to place radioactive seeds in the process called brachytherapy to treat cancer may be guided by techniques similar to those in the biopsy example above.

In another example, the subject matter described herein may be used for shape measurement of cortical and subcortical brain structures. The shapes of some structures in the brain are thought to be correlated with certain neurological conditions. The volume and shape properties of subcortical and cortical brain structures seen in MR images associated with schizophrenia and schizotypal disorders in adults. For example, the subject matter described herein may be used to investigate subcortical structures in MR images across many years starting from childhood in individuals who have been determined to be at risk for autism. Studies are being performed to monitor shape changes over time and to correlate these changes with clinical symptoms and for improving disease therapy.

In another example, the subject matter described herein may be used for improving the treatment of arthritic knee cartilage, such as developing methods for measuring the effect of arthritis drugs on the pattern of depths and curvatures of knee cartilage imaged in MRI.

In another example, the subject matter described herein may be used for creating a beating heart model to evaluate muscle damage. In one scenario, m-rep models of the beating heart of patients with ischemic disease (reduced blood flow to the heart muscle) may be used to localize regions of muscle where flow is reduced and determine how seriously the muscle is affected by comparison with a trained m-rep model of the normal beating heart. The models, made from so-called 4D images (3D plus time), can be generated by specialized CT, MR, and US technologies, will be investigated to. If successful this would be a safe non-invasive procedure to evaluate patients with ischemia and plan appropriate treatment.

In another example, the subject matter described herein may be used for studying and treating chronic obstructive pulmonary disease (COPD). M-reps may be used to study the progression of COPD in patients by automatically segmenting images of lungs using m-reps and CT images acquired at various parts of the breathing cycle. The shape measurement properties of m-reps may be used to localize and measure the volume of obstructed lung tissue.

In another example, the subject matter described herein may be used to improve treatment of tumors in the lung and in the liver that undergo motion and shape change while the patient is breathing during treatment. M-reps may be used to segment a target object and nearby organs in CT images acquired at multiple intervals over multiple respiratory cycles. A 4D model may then be built from the segmentations to predict changes across the patient's breathing cycle and to account for these changes during planning and treatment delivery.

In yet another example, the subject matter described herein may be used for improving radiation treatment planning of cancer in the head and neck. For example, m-reps may be used for planning the radiation treatment of tumors in the head and neck, a region where 15 or more objects on each side of the head and neck, together with lymphatic system sub-regions, are critically important anatomical structures.

Other potential applications include, but are not limited to, computer-aided design, simulated stress testing of critical manufacturing and construction components, and animated cartoons. It is appreciated that these applications are mentioned here only to underscore the wide range of potential product areas. The foregoing has included several ongoing or planned medical research projects where the subject matter described herein may be used either as a method to extract anatomical objects in medical images, as a statistically trained shape ruler, that is, as a way to measure and discriminate based on shape statistics, e.g., to distinguish one class of shapes (normal) from other classes (diseased), or both.

ADVANTAGES

The subject matter described herein may overcome the shortcoming with the prior art by mapping cancerous regions from non-ultrasound images to TRUS biopsy images in order to display visible targets, allowing the physician to more accurately aim his/her instrument. The net benefit to patients will be reduction in the number of repeat biopsies; easing of the mental stress related to the uncertainty of whether a negative biopsy is false, or whether a low Gleason score is falsely low; better data on which to base treatment decisions; and overall improvement in quality of life. Moreover, health care costs associated with repeat biopsies should be reduced.

The subject matter described herein may eliminate almost all human interaction by automatically extracting the patient model, and it does so in a way that is free from unwanted user variability.

The subject matter described herein may accurately model the deformations in the prostate caused by intra-rectal probes during the imaging studies and biopsy procedure, and to handle the different image properties between the TRUS and MR images.

Furthermore, it is appreciated that the subject matter described herein may be applicable to all of diagnostic, surgical, and other therapeutic interventions.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for mapping a model of an object comprising an anatomical structure in one image to image data of the object in another image, the method comprising:
    creating an initial medial representation object model (m-rep) of an object comprising an anatomical structure based on image data of at least a first instance of the object;
    creating a patient-specific m-rep by deforming the initial m-rep based on planning image data of at least a second instance of the object, wherein the at least a second instance of the object is associated with the patient;
    identifying an intervention target region registered with the planning image data;
    correlating the patient-specific m-rep and the intervention target region to intervention-guiding image data of the at least a second instance of the object; and
    simultaneously displaying the patient-specific m-rep, the intervention target region, and the intervention-guiding image data, wherein the patient-specific m-rep and the intervention target region are overlaid on the intervention-guiding image data.

2. The method of claim 1 comprising identifying the intervention target region in the intervention-guiding image data using a mapping derived from a transformation between an m-rep in the planning image data and an m-rep in the intervention-guiding image data.

3. The method of claim 1 wherein the planning image data includes magnetic resonance imaging (MRI) data and magnetic resonance spectroscopy imaging (MRSI) data, wherein the MRSI data includes an image registered with the MRI data for determining the intervention target region.

4. The method of claim 1 wherein the intervention-guiding image data includes one or more of ultrasound (US) image data and transrectal ultrasound (TRUS) image data.

5. The method of claim 1 wherein the anatomical structure includes one of a bladder, a prostate, a heart, a brain structure, a liver, and a lung.

6. The method of claim 1 wherein creating the initial m-rep or creating the patient-specific m-rep includes limiting modes of shape variability of the object to anatomically possible variations.

7. The method of claim 1 wherein creating at least one of an initial m-rep and a patient-specific m-rep includes using principal geodesic analysis (PGA) to parameterize the modes of shape variability of the object.

8. The method of claim 1 wherein creating the initial m-rep and or creating the patient-specific m-rep includes using a finite element method (FEM) to simulate and model possible deformations of the object.

9. The method of claim 1 wherein creating the initial m-rep includes deforming the initial m-rep based on training data for the object and wherein deforming the initial m-rep or deforming the patient specific m-rep includes deforming the m-rep based on image intensity values and wherein regional intensity quantile functions and principal component analysis are used to measure the match of the m-rep being deformed to either a planning image or an intervention-guiding image.

10. The method of claim 1 comprising pre-compiling a plurality of finite element method (FEM)-based shape variation scenarios and, during an intervention procedure wherein the object is deformed, performing a lookup for a matching shape variation scenario for the object deformation.

11. The method of claim 1 comprising computing a finite element method (FEM)-based shape deformation simulation based on the deformation of the object during a biopsy procedure.

12. The method of claim 1 comprising using the overlaid, displayed image data for guiding a surgical instrument during surgery.

13. The method of claim 1 comprising using the simultaneously displayed, overlaid patient specific m-rep for shape measurement of cortical and subcortical brain structures.

14. The method of claim 1 comprising using the simultaneously displayed, overlaid patient specific m-rep for creating a beating heart model to evaluate muscle damage.

15. The method of claim 1 comprising using the simultaneously displayed, overlaid patient specific m-rep to monitor or detect chronic obstructive pulmonary disease (COPD).

16. The method of claim 1 comprising using the simultaneously displayed, overlaid patient specific m-rep to perform radiation treatment for an anatomical structure under respiratory motion.

17. The method of claim 1 comprising using the simultaneously displayed, overlaid patient specific m-rep for image-guided prostate biopsy.

18. The method of claim 1 comprising using the simultaneously displayed, overlaid patient specific m-rep for image-guided brachytherapy, including image-guided prostate brachytherapy.

19. The method of claim 1 comprising using the simultaneously displayed, overlaid patient specific m-rep for radiation treatment planning of cancer in the head and neck.

20. The method of claim 1 wherein creating a patient-specific m-rep includes creating a patient-specific atlas of the object shape and internal suspicious regions.

21. A system for mapping a planning-image model of an object comprising an anatomical structure to intervention-guiding object image data, the system comprising:
an object model generator for creating a medial representation object model (m-rep) of an object comprising an anatomical structure and for identifying an intervention target region within the object based on planning image data of at least a first instance of the object; and
an object model deformation and mapping module for correlating the m-rep and the intervention target region to intervention-guiding image data of the at least a first instance of the object, deformed from the planning image, wherein the object model deformation and mapping module is configured to simultaneously display the patient-specific m-rep, the intervention target region, and the intervention-guiding image data, wherein the patient-specific m-rep is overlaid on the intervention-guiding image data.

22. The system of claim 21 wherein the object model generator is configured to generate the m-rep based on one or more of magnetic resonance imaging (MRI) data and computed tomography (CT) image data.

23. The system of claim 21 wherein the object model deformation and mapping module is configured to correlate the m-rep to one or more of ultrasound (US) image data and transrectal ultrasound (TRUS) image data.

24. The system of claim 21 wherein the object model generator is configured to create the m-rep based on one of a bladder, a prostate, a heart, a brain structure, a liver, and a lung.

25. The system of claim 21 wherein the object model generator is configured to limit the modes of shape variability of the object model to anatomically possible variations.

26. The system of claim 21 wherein the object model generator is configured to use principal geodesic analysis (PGA) to parameterize the modes of shape variability of the object.

27. The system of claim 21 wherein the object model generator is configured to use finite element method (FEM) to simulate and model possible deformations of the object.

28. The system of claim 21 wherein the object model deformation and mapping module is configured to deform the object model based on image intensity values.

29. The system of claim 21 wherein the object model deformation and mapping module is configured to pre-compile a plurality of finite element method (FEM)-based shape variation scenarios and, during a biopsy procedure wherein the object is deformed, perform a lookup for a matching shape variation scenario for the object deformation.

30. The system of claim 21 wherein the object model deformation and mapping module is configured to compute a finite element method (FEM)-based shape deformation simulation based on the deformation of the object during a biopsy procedure.

31. The system of claim 21 wherein the object model deformation and mapping module is configured to simultaneously display and overlay the m-rep and an intervention target region on the intervention-guiding image data and use the overlaid, displayed image data for guiding a surgical instrument during surgery.

32. The system of claim 31 wherein the simultaneously displayed, overlaid m-rep is used for shape measurement of cortical and subcortical brain structures.

33. The system of claim 31 wherein the simultaneously displayed, overlaid m-rep is used to monitor knee cartilage under treatment for arthritis.

34. The system of claim 31 wherein the simultaneously displayed, overlaid m-rep is used for creating a beating heart model to evaluate muscle damage.

35. The system of claim 31 wherein the simultaneously displayed, overlaid m-rep is used to monitor or detect chronic obstructive pulmonary disease (COPD).

36. The system of claim 31 wherein the simultaneously displayed, overlaid m-rep is used to perform radiation treatment for an anatomical structure under respiratory motion.

37. The system of claim 31 wherein the simultaneously displayed, overlaid m-rep is used for radiation treatment planning of cancer in the head and neck.

38. The system of claim 31 wherein the simultaneously displayed, overlaid m-rep is used for image-guided prostate biopsy.

39. The system of claim 31 wherein the simultaneously displayed, overlaid m-rep is used for image-guided prostate brachytherapy.

40. The system of claim 21 wherein the object model generator is configured to create a patient-specific m-rep and a patient-specific atlas of the object shape and to represent internal suspicious regions in object-relative coordinates within the m-rep.

41. A computer readable medium comprising computer executable instructions that when executed by a processor of a computer performs steps comprising:

creating an initial medial representation object model (m-rep) of an object comprising an anatomical structure based on image data of at least a first instance of the object;

creating a patient-specific m-rep by deforming the initial m-rep based on planning image data of at least a second instance of the object, wherein the at least second instance of the object is associated with the patient;

identifying an intervention target region registered with the planning image data;

correlating the patient-specific m-rep and the intervention target region to intervention-guiding image data of the at least a second instance of the object; and simultaneously displaying the patient-specific m-rep, the intervention target region, and the intervention-guiding image data, wherein the patient-specific m-rep and the intervention target region are overlaid on the intervention-guiding image data.

* * * * *

UNITED STATES PATENT AND TRADEMARK OFFICE
CERTIFICATE OF CORRECTION

PATENT NO.        : 8,666,128 B2                                     Page 1 of 1
APPLICATION NO.   : 12/738572
DATED             : March 4, 2014
INVENTOR(S)       : Chaney et al.

It is certified that error appears in the above-identified patent and that said Letters Patent is hereby corrected as shown below:

In the Claims

Column 22, line 7, Claim 21
  replace "patient-specific m-rep"
  with --m-rep--

Column 22, line 9, Claim 21
  replace "patient-specific m-rep"
  with --m-rep--

Column 22, line 49, Claim 31
  replace "and an intervention"
  with --and the intervention--

Signed and Sealed this
Thirtieth Day of June, 2015

Michelle K. Lee
*Director of the United States Patent and Trademark Office*